(12) United States Patent
Ma et al.

(10) Patent No.: US 11,535,602 B1
(45) Date of Patent: Dec. 27, 2022

(54) NITROGEN-CONTAINING COMPOUND, ELECTRONIC ELEMENT AND ELECTRONIC APPARATUS

(71) Applicant: Shaanxi Lighte Optoelectronics Material Co., Ltd., Xi'an (CN)

(72) Inventors: Tiantian Ma, Xi'an (CN); Lei Yang, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/622,744

(22) PCT Filed: Dec. 28, 2020

(86) PCT No.: PCT/CN2020/140289
§ 371 (c)(1),
(2) Date: Dec. 24, 2021

(87) PCT Pub. No.: WO2021/136197
PCT Pub. Date: Jul. 8, 2021

(30) Foreign Application Priority Data

Dec. 30, 2019 (CN) .......................... 201911404298.1

(51) Int. Cl.
*C07D 307/91* (2006.01)
*C07D 333/76* (2006.01)
(Continued)

(52) U.S. Cl.
CPC ......... *C07D 307/91* (2013.01); *C07D 333/76* (2013.01); *H01L 51/0061* (2013.01);
(Continued)

(58) Field of Classification Search
CPC .. C07D 307/91; C07D 333/76; H01L 51/0061
See application file for complete search history.

(56) References Cited

FOREIGN PATENT DOCUMENTS

| CN | 110183332 A | 8/2019 |
|---|---|---|
| CN | 110885320 A | 3/2020 |

(Continued)

OTHER PUBLICATIONS

International Search Report from corresponding International Application No. PCT/CN2020/140289, dated Apr. 1, 2021, 4 pages.

*Primary Examiner* — Anthony Ho
(74) *Attorney, Agent, or Firm* — Tucker Ellis LLP

(57) ABSTRACT

The present application relates to the technical field of organic materials, and provides a nitrogen-containing compound, an electronic element and an electronic apparatus. The structure of the nitrogen-containing compound is shown as Chemical formula 1. The nitrogen-containing compound can improve the performance of the electronic element. Ar is II, and X is selected from O or S; $L_1$ is III, and in $L_1$, "#" represents a connection point between the phenylene of $L_1$ and N, and "##" represents a connection point between the phenylene of $L_1$ and IV; $L_2$ is V, and in $L_2$, "#" represents a connection point between the phenylene of $L_2$ and N, and "##" represents a connection point between the phenylene of $L_2$ and $R_4$.

(Continued)

-continued

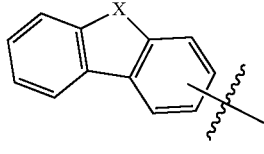

II

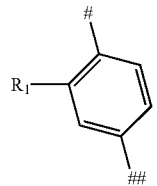

III

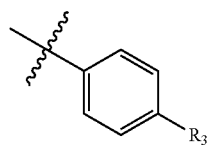

IV

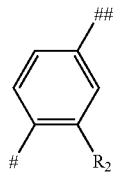

V

14 Claims, 3 Drawing Sheets

(51) Int. Cl.
 *H01L 51/50* (2006.01)
 *H01L 51/00* (2006.01)
(52) U.S. Cl.
 CPC ...... *H01L 51/0073* (2013.01); *H01L 51/0074* (2013.01); *H01L 51/5064* (2013.01)
(56) References Cited

FOREIGN PATENT DOCUMENTS

CN 111153880 A 5/2020
KR 20180078177 A 7/2018

NITROGEN-CONTAINING COMPOUND, ELECTRONIC ELEMENT AND ELECTRONIC APPARATUS

CROSS REFERENCE TO RELATED APPLICATIONS

This application claims priority of Chinese patent application with the application number of CN201911404298.1, filed on Dec. 30, 2019, which is incorporated herein by reference in its entirety.

TECHNICAL FIELD

The present disclosure relates to the technical field of organic materials, and in particular relates to a nitrogen-containing compound, an electronic element and an electronic apparatus containing the nitrogen-containing compound.

BACKGROUND

With the development of the electronic technology and the progress of material science, the application range of electronic elements for realizing electroluminescence or photoelectric conversion has become more and more wide. These electronic elements, such as organic electroluminescent devices or photoelectric conversion devices, usually include a cathode and an anode which are arranged oppositely, and a functional layer arranged between the cathode and the anode. The functional layer consists of a plurality of organic or inorganic membrane layers, and generally includes an energy conversion layer, a hole transporting layer located between the energy conversion layer and the anode, and an electron transporting layer located between the energy conversion layer and the cathode.

For example, when the electronic element is an organic electroluminescent device, the element generally includes an anode, a hole transporting layer, an organic light-emitting layer serving as the energy conversion layer, an electron transporting layer and a cathode which are sequentially stacked. When the voltage is applied to the cathode and the anode, the two electrodes generate an electric field. Under the action of the electric field, electrons at the cathode side move towards the organic light-emitting layer, holes at the anode side move towards the organic light-emitting layer, the electrons and the holes are combined at the organic light-emitting layer to form excitons. The excitons are in an excited state to release energy outwards, so that the organic light-emitting layer emits light outwards.

Although there are materials that can be applied to the hole transporting layer of the organic electroluminescent device, it is still necessary to continuously research and develop a novel material so as to further improve the performance of the electronic element.

The above information disclosed in the background is only used to reinforce the understanding of the background of the present disclosure, so the information may include information which does not constitute the prior art known to those of ordinary skill in the art.

SUMMARY

An objective of the present disclosure is to provide a nitrogen-containing compound, an electronic element and an electronic apparatus. The nitrogen-containing compound can improve the performance of the electronic element.

To achieve the above inventive objective, the present disclosure adopts the following technical solution.

According to a first aspect of the present disclosure, a nitrogen-containing compound is provided. The structure of the nitrogen-containing compound is shown as Chemical formula 1.

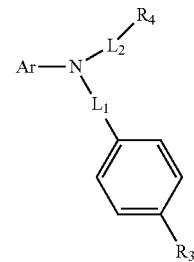

Chemical formula 1 wherein Ar is

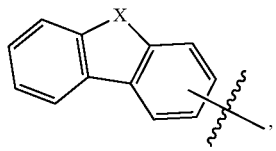

and X is selected from O or S;

$L_1$ is

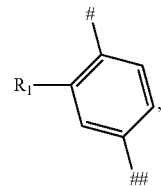

and in $L_1$, "#" represents a connection point between the phenylene of $L_1$ and N, and "##" represents a connection point between the phenylene of $L_1$ and

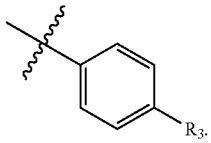

$L_2$ is

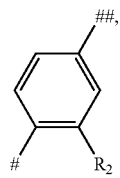

and in $L_2$, "#" represents a connection point between the phenylene of $L_2$ and N, and "##" represents a connection point between the phenylene of $L_2$ and $R_4$.

$R_1$ is selected from methyl or phenyl. $R_2$ is selected from methyl or phenyl.

$R_3$ is selected from H and the groups shown in CA1 to CA10. $R_4$ is selected from phenyl and the substituents shown in CA1 to CA10, and only one of $R_3$ and $R_4$ is selected from the substituents shown in CA1 to CA10. Wherein the structures of CA1 to CA10 are as follows:

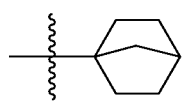

CA1

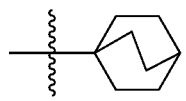

CA2

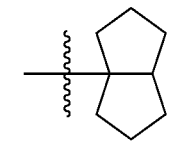

CA3

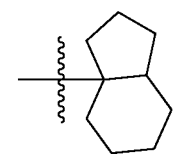

CA4

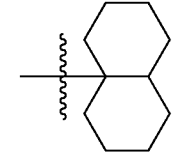

CA5

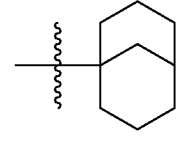

CA6

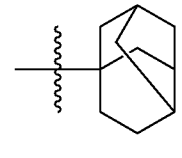

CA7

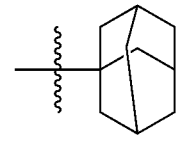

CA8

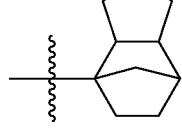

CA9

-continued

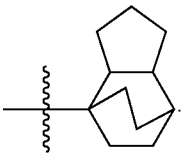

CA10

According to a second aspect of the present disclosure, an electronic element is provided. The electronic element comprises an anode and a cathode which are arranged oppositely, and a functional layer arranged between the anode and the cathode, wherein the functional layer contains the nitrogen-containing compound described in the first aspect of the present disclosure.

According to a third aspect of the present disclosure, an electronic apparatus is provided. The electronic apparatus comprises the electronic element described in the second aspect of the present application.

The compound of the present application has a dibenzofuran group or a dibenzothiophene group, which has strong electron dissociation energy, so the HOMO energy level of the nitrogen-containing compound can be effectively reduced, this allows the hole transporting layer to inject holes into the organic light-emitting layer serving as the energy conversion layer more smoothly, or allows the photoelectric conversion layer serving as the energy conversion layer to inject holes into the electron transporting layer more smoothly, and the nitrogen-containing compound has good hole transporting efficiency. The introduction of the dibenzofuran group or the dibenzothiophene group may increase the conjugate plane of the nitrogen-containing compound of the present application, and may also cause intermolecular stacking and crystallization to shorten the life of the device, but by introducing the cycloalkane structure with large steric hindrance, the stacking effect of the compound can be effectively reduced, and the film-forming performance of the nitrogen-containing compound can be improved. More importantly, in the compound of the present application, a specific substituent is introduced at the ortho-position of the nitrogen atom on the aryl group, so that the planarity of the triarylamine core group can be reduced, the HOMO energy level can be further improved, and the intermolecular stacking effect can be reduced. Therefore, the nitrogen-containing compound of the present application is suitable for the hole transporting layer of the organic electroluminescent device, particularly suitable for the second hole transporting layer of the organic electroluminescent device, so that the driving voltage drop of the organic electroluminescent device can be reduced, the current efficiency, the power efficiency and the external quantum efficiency of the organic electroluminescent device can be improved, and the life of the organic electroluminescent device can be prolonged.

BRIEF DESCRIPTION OF THE DRAWINGS

The above and other features and advantages of the present disclosure will become more apparent by describing the exemplary embodiments in detail with reference to the accompanying drawings.

Figure 1:
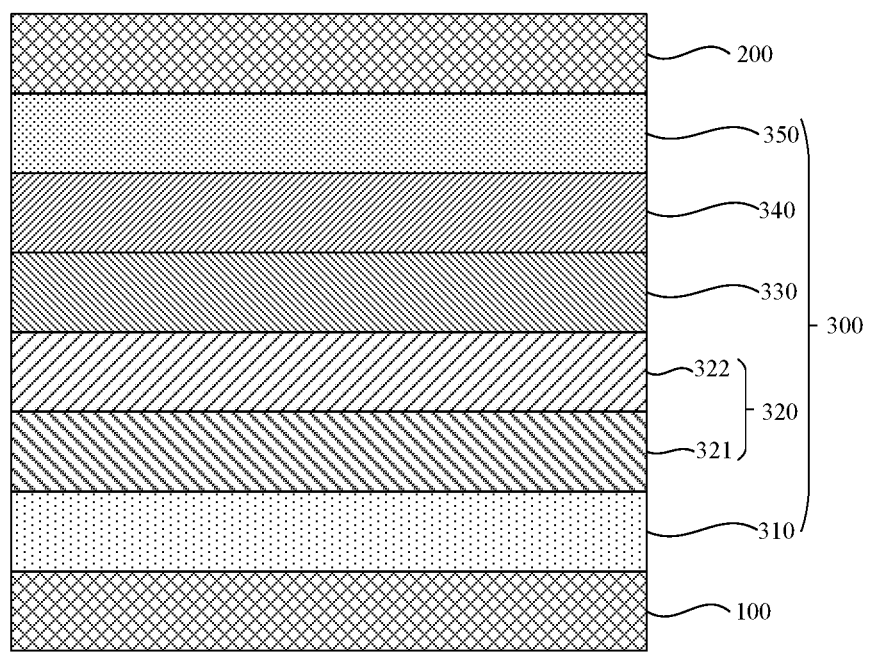
FIG. 1 is a structural schematic diagram of an organic electroluminescent device according to the embodiments of the present disclosure.

Description of reference signs of main element in the drawings is as follows:

100. Anode; 200. Cathode; 300. Functional layer; 310. Hole injecting layer; 320. Hole transporting layer; 321. First hole transporting layer; 322. Second hole transporting layer; 330. Organic light-emitting layer; 340. Electron transporting layer; 350. Electron injecting layer; 360. Photoelectric conversion layer; 400. Electronic apparatus; 500. Electronic apparatus.

DETAILED DESCRIPTION

Exemplary embodiments are now described more comprehensively with reference to the accompanying drawings. However, the exemplary embodiments can be implemented in various forms and should not be construed as being limited to the examples described herein; on the contrary, these embodiments are provided, so that the present disclosure will be more comprehensive and complete, and the concept of the exemplary embodiments will be completely conveyed to those skilled in the art. The features, structures, or characteristics described may be combined in one or more embodiments in any suitable manner. In the following description, numerous specific details are provided to give a sufficient understanding of the embodiments of the present disclosure.

In the drawings, the area and layers thickness may be exaggerated for clarity. In the drawings, the same reference sign denotes the same or similar structure, and thus their detailed description will be omitted.

In the present disclosure, the aryl group refers to optional functional groups or substituents derived from aromatic rings. The aryl group may be a monocyclic aryl group or a polycyclic aryl group. In other words, the aryl group may be a monocyclic aryl group, a fused aryl group, two or more monocyclic aryl groups conjugated through carbon-carbon bonds, a monocyclic aryl group and a fused aryl group conjugated through carbon-carbon bonds, and two or more fused aryl groups conjugated through carbon-carbon bonds. That is, the two or more aryl groups conjugated through carbon-carbon bonds may also be regarded as aryl groups of the present disclosure. Among them, the aryl group does not contain heteroatoms such as B, N, O, S or P. For example, biphenyl and terphenyl and the like are the aryl groups in the present disclosure. The examples of the aryl group include, but are not limited to, phenyl, naphthyl, fluorenyl, anthryl, phenanthryl, biphenyl, terphenyl, quaterphenyl, pyrenyl, chrysenyl and the like.

In the present disclosure, the heteroaryl group may be a heteroaryl group including at least one of B, O, N, P, Si and S as a heteroatom. The heteroaryl group may be a monocyclic heteroaryl group or a polycyclic heteroaryl group. In other words, the heteroaryl group may be a single aromatic ring system, and may also be a plurality of aromatic ring systems conjugated through carbon-carbon bonds; and any one aromatic ring system is an aromatic monocyclic ring or an aromatic fused ring. The specific examples of the heteroaryl group include, but are not limited to, thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, N-phenylcarbazolyl, N-pyridylcarbazolyl, N-methylcarbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, dibenzosilyl, dibenzofuranyl, phenyl-substituted dibenzofuranyl, dibenzofuranyl-substituted phenyl, and the like.

In the present disclosure, the description manners "are each independently . . . ", ". . . are respectively independently" and " . . . are independently selected from" are interchangeable and should be understood in a broad sense, which may mean that the specific options expressed between the same symbols in different groups do not affect each other, or may mean that the specific options expressed between the same symbols in the same group do not affect each other.

In the present disclosure, the non-located connection bond refers to a single bond "┼" extending from the ring system, which means that one end of the connection bond may be connected to any position in the ring system through which the bond penetrates and the other end may be connected to other parts of the compound molecule. For example, as shown in the following formula (X'), phenanthryl represented by the formula (X') is connected to other positions of the molecule through a non-located connection bond extending from the middle of the benzene ring at one side, and its meaning includes any possible connection manner shown in formulae (X'-1) to (X'-4).

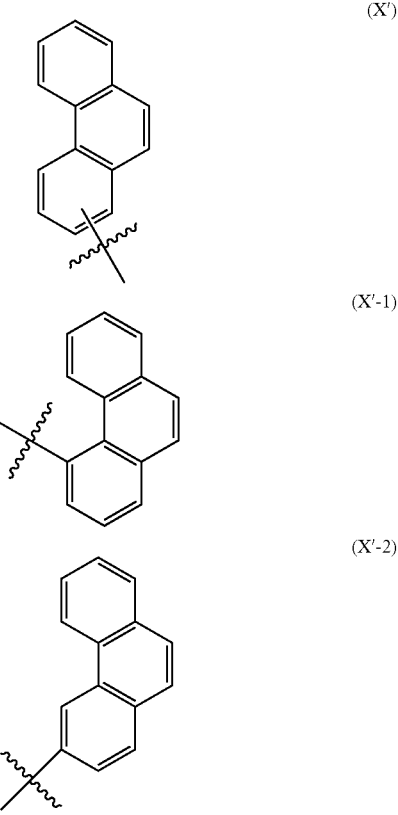

-continued

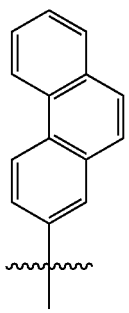
(X'-3)

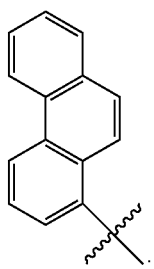
(X'-4)

According to a first aspect, the present disclosure provides a nitrogen-containing compound having a structure shown as follows:

Chemical formula 1

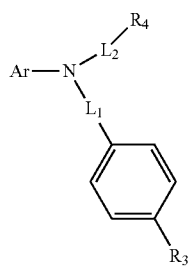

wherein Ar is

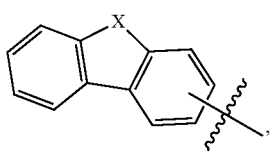

and X is selected from O or S, that is, Ar is

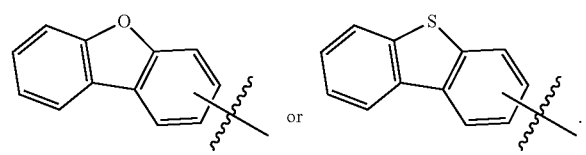

$L_1$ is

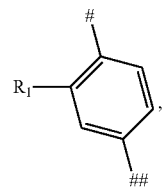

and in $L_1$, and "##" represents a connection point between the phenylene of $L_1$ and

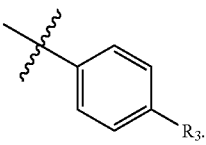

$L_2$ is

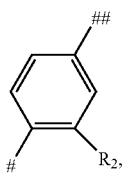

and in $L_2$, "#" represents a connection point between the phenylene of $L_2$ and N, and "##" represents a connection point between the phenylene of $L_2$ and $R_4$.

$R_1$ is selected from methyl or phenyl; $R_2$ is selected from methyl or phenyl.

$R_3$ is selected from H and the groups shown in CA1 to CA10; $R_4$ is selected from phenyl and the substituents shown in CA1 to CA10; only one of $R_3$ and $R_4$ is selected from the substituents shown in CA1 to CA10; where the structures of CA1 to CA10 are as follows:

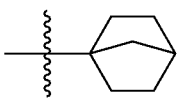
CA1

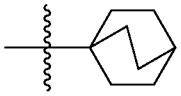
CA2

CA3

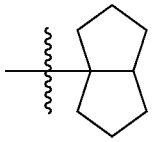

CA4

-continued

CA5 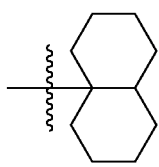

CA6 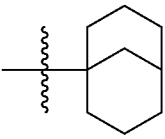

CA7 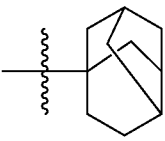

CA8 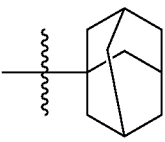

CA9 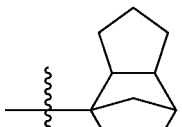

CA10 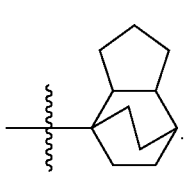

For example, in the compound

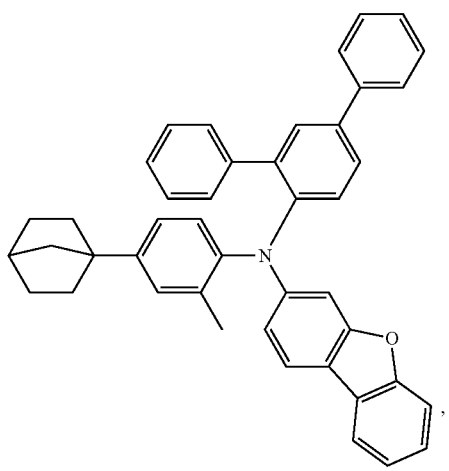 [SMILES: Cc1cc(C23CCC(CC2)C3)ccc1N(c1ccc2c(c1)oc1ccccc12)c1ccc(-c2ccccc2)cc1-c1ccccc1]

Ar is

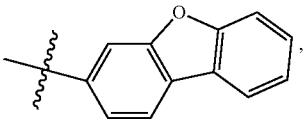 [SMILES: *c1ccc2c(c1)oc1ccccc12]

$L_1$ is

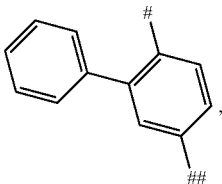

$L_2$ is

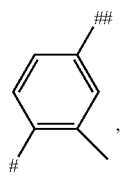

$R_1$ is phenyl, $R_2$ is methyl, $R_3$ is H, and $R_4$ is

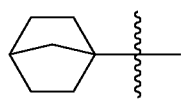

The nitrogen-containing compound of the present disclosure has a dibenzofuran group or a dibenzothiophene group, and the dibenzofuran group or the dibenzothiophene group has strong electron dissociation energy, so the HOMO energy level of the nitrogen-containing compound can be effectively reduced, this allows the hole transporting layer to inject holes into the organic light-emitting layer serving as the energy conversion layer more smoothly, or allows the photoelectric conversion layer serving as the energy conversion layer to inject holes into the electron transporting layer more smoothly, and the nitrogen-containing compound has good hole transporting efficiency. In this way, the voltage performance and the efficiency performance of the electronic element applying the nitrogen-containing compound can be effectively improved. For example, the luminous efficiency of the organic electroluminescent device can be improved, the driving voltage of the organic electroluminescent device can be reduced, the photoelectric efficiency and the open-circuit voltage of the photoelectric conversion device can also be improved. The introduction of the dibenzofuran group or the dibenzothiophene group may increase a conjugate plane of the nitrogen-containing compound of the present application, and may also cause intermolecular stacking and crystallization to shorten the life of the device. In order to overcome the possible adverse effect of the dibenzofuran group or the dibenzothiophene group, part of the nitrogen-containing compound of the present application also introduces a cycloalkane structure with large steric hindrance, and the cycloalkane group can effectively reduce the stacking effect of the nitrogen-containing compound of the present application and can improve the film-forming performance of the nitrogen-containing compound. The preparation and test results of the organic electroluminescent device show that the introduction of the cycloalkane group prolongs the life of the organic electroluminescent device, which indicates that the adverse effect of the dibenzofuran group or the dibenzothiophene group is overcome, the film-forming performance of the nitrogen-containing compound is effectively improved, the planarity of the nitrogen-containing compound itself is reduced, particularly the intermolecular stacking effect of the nitrogen-containing compound is reduced, so that the life of the electronic element applying the nitrogen-containing compound of the present application is prolonged. Therefore, the nitrogen-containing compound of the present application has better hole transporting performance, lower HOMO energy level, lower intermolecular stacking effects and more excellent film-forming performance, and can improve the voltage performance, efficiency performance and life performance of the electronic element such as the photoelectric conversion device and the electroluminescent device.

More importantly, in the compound of the present application, a specific substituent is introduced at the ortho-position of the nitrogen atom on the aryl group, so that the planarity of the triarylamine core group can be reduced, the HOMO energy level can be further improved, and the intermolecular stacking effect can be reduced. Therefore, the nitrogen-containing compound of the present application is suitable for the hole transporting layer of the organic electroluminescent device, particularly suitable for the second hole transporting layer of the organic electroluminescent device, so that the driving voltage drop of the organic electroluminescent device can be reduced, the current efficiency, the power efficiency and the external quantum efficiency of the organic electroluminescent device can be improved, and the life of the organic electroluminescent device can be prolonged.

Optionally, Ar is selected from 2-DBF, 3-DBF, 2-DBT or 3-DBT, wherein the structural formulas of 2-DBF, 3-DBF, 2-DBT and 3-DBT are as follows:

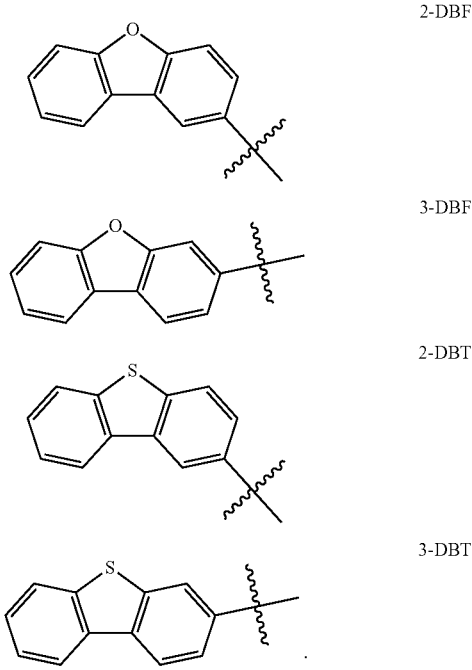

Optionally, the nitrogen-containing compound is selected from the group consisting of various compounds listed in the Table 1:

TABLE 1

| Substituent of compound | Ar | $L_1$ | $R_3$ | $R_4$ | $L_2$ |
|---|---|---|---|---|---|
| Compound 111 | 2-DBF | (structure) | CA2 | Ph | (structure) |
| Compound 112 | 2-DBF | (structure) | CA3 | Ph | (structure) |
| Compound 113 | 2-DBF | (structure) | CA4 | Ph | (structure) |

TABLE 1-continued
| Substituent of compound | Ar | L₁ | R₃ | R₄ | L₂ |
|---|---|---|---|---|---|
| Compound 114 | 2-DBF | 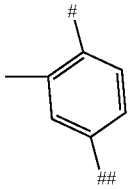 | CA5 | Ph | 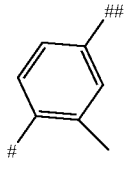 |
| Compound 115 | 2-DBF | 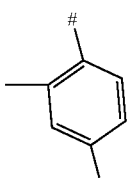 | CA6 | Ph | 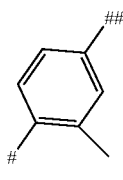 |
| Compound 116 | 2-DBF | 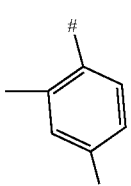 | CA9 | Ph | 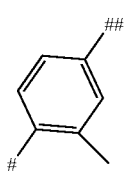 |
| Compound 117 | 2-DBF | 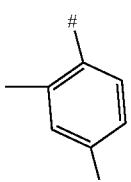 | CA10 | Ph | 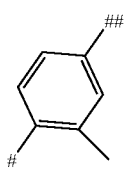 |
| Compound 133 | 2-DBF | 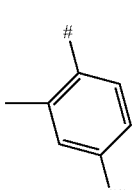 | CA1 | Ph | 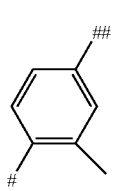 |
| Compound 155 | 2-DBF | 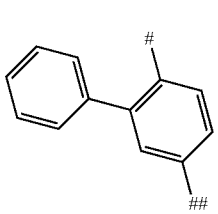 | CA1 | Ph | 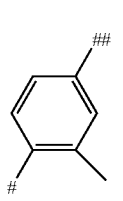 |
| Compound 156 | 2-DBF | 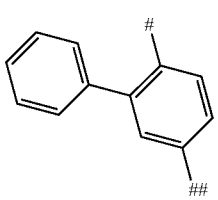 | CA2 | Ph | 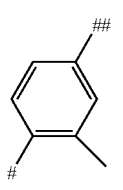 |

TABLE 1-continued

| Substituent of compound | Ar | L₁ | R₃ | R₄ | L₂ |
|---|---|---|---|---|---|
| Compound 157 | 2-DBF | [biphenyl structure with # and ##] | CA3 | Ph | [dimethylphenyl structure with # and ##] |
| Compound 158 | 2-DBF | [biphenyl structure with # and ##] | CA4 | Ph | [dimethylphenyl structure with # and ##] |
| Compound 159 | 2-DBF | [biphenyl structure with # and ##] | CA5 | Ph | [dimethylphenyl structure with # and ##] |
| Compound 160 | 2-DBF | [biphenyl structure with # and ##] | CA6 | Ph | [dimethylphenyl structure with # and ##] |
| Compound 161 | 2-DBF | [biphenyl structure with # and ##] | CA7 | Ph | [dimethylphenyl structure with # and ##] |
| Compound 162 | 2-DBF | [biphenyl structure with # and ##] | CA8 | Ph | [dimethylphenyl structure with # and ##] |
| Compound 163 | 2-DBF | [biphenyl structure with # and ##] | CA9 | Ph | [dimethylphenyl structure with # and ##] |
| Compound 164 | 2-DBF | [biphenyl structure with # and ##] | CA10 | Ph | [dimethylphenyl structure with # and ##] |

TABLE 1-continued

| Substituent of compound | Ar | L₁ | R₃ | R₄ | L₂ |
|---|---|---|---|---|---|
| Compound 167 | 2-DBF | (2,4-disubstituted methylphenyl with # at 1, ## at 4) | CA1 | Ph | (biphenyl linker with ## and #) |
| Compound 168 | 2-DBF | (2,4-disubstituted methylphenyl with # at 1, ## at 4) | CA2 | Ph | (biphenyl linker with ## and #) |
| Compound 169 | 2-DBF | (2,4-disubstituted methylphenyl with # at 1, ## at 4) | CA3 | Ph | (biphenyl linker with ## and #) |
| Compound 170 | 2-DBF | (2,4-disubstituted methylphenyl with # at 1, ## at 4) | CA4 | Ph | (biphenyl linker with ## and #) |
| Compound 171 | 2-DBF | (2,4-disubstituted methylphenyl with # at 1, ## at 4) | CA5 | Ph | (biphenyl linker with ## and #) |
| Compound 172 | 2-DBF | (2,4-disubstituted methylphenyl with # at 1, ## at 4) | CA6 | Ph | (biphenyl linker with ## and #) |

TABLE 1-continued

| Substituent of compound | Ar | L₁ | R₃ | R₄ | L₂ |
|---|---|---|---|---|---|
| Compound 173 | 2-DBF | (methylphenylene) | CA8 | Ph | (biphenylene) |
| Compound 174 | 2-DBF | (methylphenylene) | CA9 | Ph | (biphenylene) |
| Compound 176 | 2-DBF | (biphenylene) | CA1 | Ph | (biphenylene) |
| Compound 177 | 2-DBF | (biphenylene) | CA2 | Ph | (biphenylene) |
| Compound 178 | 2-DBF | (biphenylene) | CA3 | Ph | (biphenylene) |
| Compound 179 | 2-DBF | (biphenylene) | CA5 | Ph | (biphenylene) |

TABLE 1-continued

| Substituent of compound | Ar | L₁ | R₃ | R₄ | L₂ |
|---|---|---|---|---|---|
| Compound 180 | 2-DBF | (biphenyl structure) | CA6 | Ph | (biphenyl structure) |
| Compound 181 | 2-DBF | (biphenyl structure) | CA7 | Ph | (biphenyl structure) |
| Compound 182 | 2-DBF | (biphenyl structure) | CA8 | Ph | (biphenyl structure) |
| Compound 183 | 2-DBF | (biphenyl structure) | CA9 | Ph | (biphenyl structure) |
| Compound 184 | 2-DBF | (biphenyl structure) | CA10 | Ph | (biphenyl structure) |
| Compound 199 | 2-DBF | (methylphenyl structure) | CA7 | Ph | (biphenyl structure) |

TABLE 1-continued

| Substituent of compound | Ar | L₁ | R₃ | R₄ | L₂ |
|---|---|---|---|---|---|
| Compound 208 | 2-DBF | (biphenyl structure with # and ##) | CA4 | Ph | (biphenyl structure with ## and #) |
| Compound 218 | 2-DBF | (methylphenyl structure with # and ##) | H | CA1 | (methylphenyl structure with ## and #) |
| Compound 219 | 2-DBF | (methylphenyl structure with # and ##) | H | CA2 | (methylphenyl structure with ## and #) |
| Compound 220 | 2-DBF | (methylphenyl structure with # and ##) | H | CA3 | (methylphenyl structure with ## and #) |
| Compound 221 | 2-DBF | (methylphenyl structure with # and ##) | H | CA4 | (methylphenyl structure with ## and #) |
| Compound 222 | 2-DBF | (methylphenyl structure with # and ##) | H | CA5 | (methylphenyl structure with ## and #) |
| Compound 223 | 2-DBF | (methylphenyl structure with # and ##) | H | CA6 | (methylphenyl structure with ## and #) |

TABLE 1-continued

| Substituent of compound | Ar | L₁ | R₃ | R₄ | L₂ |
|---|---|---|---|---|---|
| Compound 224 | 2-DBF | (structure) | H | CA7 | (structure) |
| Compound 225 | 2-DBF | (structure) | H | CA8 | (structure) |
| Compound 226 | 2-DBF | (structure) | H | CA9 | (structure) |
| Compound 253 | 2-DBF | (structure) | H | CA4 | (structure) |
| Compound 254 | 2-DBF | (structure) | H | CA5 | (structure) |
| Compound 255 | 2-DBF | (structure) | H | CA6 | (structure) |
| Compound 256 | 2-DBF | (structure) | H | CA7 | (structure) |
| Compound 257 | 2-DBF | (structure) | H | CA8 | (structure) |

TABLE 1-continued

| Substituent of compound | Ar | L₁ | R₃ | R₄ | L₂ |
|---|---|---|---|---|---|
| Compound 258 | 2-DBF | (biphenyl structure) | H | CA9 | (methylphenyl structure) |
| Compound 259 | 2-DBF | (biphenyl structure) | H | CA10 | (methylphenyl structure) |
| Compound 262 | 2-DBF | (methylphenyl structure) | H | CA1 | (biphenyl structure) |
| Compound 263 | 2-DBF | (methylphenyl structure) | H | CA2 | (biphenyl structure) |
| Compound 264 | 2-DBF | (methylphenyl structure) | H | CA3 | (biphenyl structure) |
| Compound 265 | 2-DBF | (methylphenyl structure) | H | CA4 | (biphenyl structure) |

TABLE 1-continued

| Substituent of compound | Ar | L₁ | R₃ | R₄ | L₂ |
|---|---|---|---|---|---|
| Compound 266 | 2-DBF | (2,4-phenylene, # at 1, ## at 4) | H | CA5 | (biphenyl linker) |
| Compound 267 | 2-DBF | (2,4-phenylene, # at 1, ## at 4) | H | CA6 | (biphenyl linker) |
| Compound 268 | 2-DBF | (2,4-phenylene, # at 1, ## at 4) | H | CA7 | (biphenyl linker) |
| Compound 269 | 2-DBF | (2,4-phenylene, # at 1, ## at 4) | H | CA8 | (biphenyl linker) |
| Compound 270 | 2-DBF | (2,4-phenylene, # at 1, ## at 4) | H | CA9 | (biphenyl linker) |
| Compound 271 | 2-DBF | (2,4-phenylene, # at 1, ## at 4) | H | CA10 | (biphenyl linker) |

TABLE 1-continued

| Substituent of compound | Ar | L₁ | R₃ | R₄ | L₂ |
|---|---|---|---|---|---|
| Compound 274 | 2-DBF | [structure] | H | CA1 | [structure] |
| Compound 275 | 2-DBF | [structure] | H | CA2 | [structure] |
| Compound 276 | 2-DBF | [structure] | H | CA3 | [structure] |
| Compound 277 | 2-DBF | [structure] | H | CA4 | [structure] |
| Compound 278 | 2-DBF | [structure] | H | CA5 | [structure] |
| Compound 279 | 2-DBF | [structure] | H | CA6 | [structure] |

TABLE 1-continued

| Substituent of compound | Ar | L₁ | R₃ | R₄ | L₂ |
|---|---|---|---|---|---|
| Compound 280 | 2-DBF | [biphenyl with # and ##] | H | CA7 | [biphenyl with ## and #] |
| Compound 281 | 2-DBF | [biphenyl with # and ##] | H | CA8 | [biphenyl with ## and #] |
| Compound 282 | 2-DBF | [biphenyl with # and ##] | H | CA9 | [biphenyl with ## and #] |
| Compound 283 | 2-DBF | [biphenyl with # and ##] | H | CA10 | [biphenyl with ## and #] |
| Compound 408 | 3-DBF | [dimethylphenyl with # and ##] | CA1 | Ph | [dimethylphenyl with ## and #] |
| Compound 409 | 3-DBF | [dimethylphenyl with # and ##] | CA2 | Ph | [dimethylphenyl with ## and #] |
| Compound 410 | 3-DBF | [dimethylphenyl with # and ##] | CA3 | Ph | [dimethylphenyl with ## and #] |

TABLE 1-continued
| Substituent of compound | Ar | L₁ | R₃ | R₄ | L₂ |
|---|---|---|---|---|---|
| Compound 411 | 3-DBF | 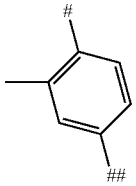 | CA6 | Ph | 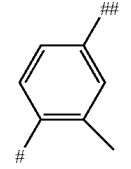 |
| Compound 412 | 3-DBF | 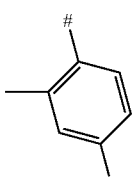 | CA7 | Ph | 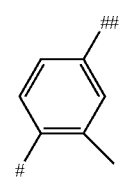 |
| Compound 413 | 3-DBF | 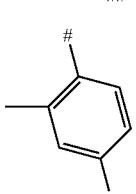 | CA8 | Ph | 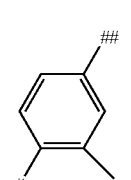 |
| Compound 414 | 3-DBF | 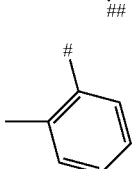 | CA9 | Ph | 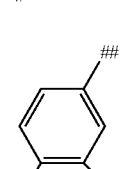 |
| Compound 451 | 3-DBF | 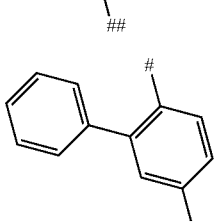 | CA1 | Ph | 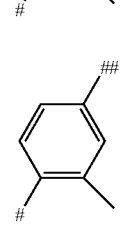 |
| Compound 452 | 3-DBF | 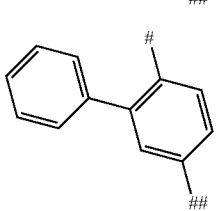 | CA2 | Ph | 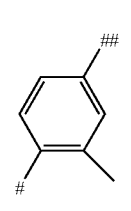 |
| Compound 453 | 3-DBF | 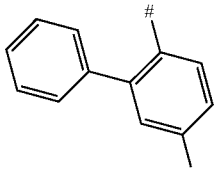 | CA3 | Ph | 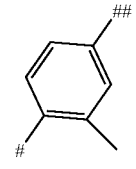 |
| Compound 454 | 3-DBF | 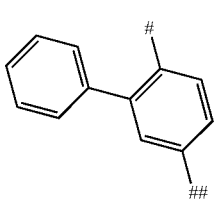 | CA4 | Ph | 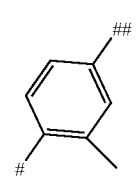 |

TABLE 1-continued

| Substituent of compound | Ar | L₁ | R₃ | R₄ | L₂ |
|---|---|---|---|---|---|
| Compound 455 | 3-DBF | (biphenyl, # upper, ## lower) | CA5 | Ph | (dimethylphenyl) |
| Compound 457 | 3-DBF | (biphenyl, # upper, ## lower) | CA7 | Ph | (dimethylphenyl) |
| Compound 458 | 3-DBF | (biphenyl, # upper, ## lower) | CA9 | Ph | (dimethylphenyl) |
| Compound 459 | 3-DBF | (biphenyl, # upper, ## lower) | CA10 | Ph | (dimethylphenyl) |
| Compound 462 | 3-DBF | (methylphenyl) | CA1 | Ph | (biphenyl) |
| Compound 463 | 3-DBF | (methylphenyl) | CA2 | Ph | (biphenyl) |
| Compound 464 | 3-DBF | (methylphenyl) | CA3 | Ph | (biphenyl) |

TABLE 1-continued

| Substituent of compound | Ar | L₁ | R₃ | R₄ | L₂ |
|---|---|---|---|---|---|
| Compound 465 | 3-DBF | (2,4-phenylene) | CA4 | Ph | (biphenyl linker) |
| Compound 466 | 3-DBF | (2,4-phenylene) | CA10 | Ph | (methylphenyl linker) |
| Compound 467 | 3-DBF | (2,4-phenylene) | CA5 | Ph | (biphenyl linker) |
| Compound 468 | 3-DBF | (2,4-phenylene) | CA8 | Ph | (biphenyl linker) |
| Compound 469 | 3-DBF | (2,4-phenylene) | CA9 | Ph | (biphenyl linker) |
| Compound 470 | 3-DBF | (2,4-phenylene) | CA10 | Ph | (biphenyl linker) |

TABLE 1-continued

| Substituent of compound | Ar | L₁ | R₃ | R₄ | L₂ |
|---|---|---|---|---|---|
| Compound 471 | 3-DBF | [biphenyl structure with # and ##] | CA1 | Ph | [biphenyl structure with ## and #] |
| Compound 472 | 3-DBF | [biphenyl structure with # and ##] | CA2 | Ph | [biphenyl structure with ## and #] |
| Compound 473 | 3-DBF | [biphenyl structure with # and ##] | CA3 | Ph | [biphenyl structure with ## and #] |
| Compound 474 | 3-DBF | [biphenyl structure with # and ##] | CA4 | Ph | [biphenyl structure with ## and #] |
| Compound 475 | 3-DBF | [biphenyl structure with # and ##] | CA5 | Ph | [biphenyl structure with ## and #] |
| Compound 476 | 3-DBF | [biphenyl structure with # and ##] | CA6 | Ph | [biphenyl structure with ## and #] |

TABLE 1-continued

| Substituent of compound | Ar | L₁ | R₃ | R₄ | L₂ |
|---|---|---|---|---|---|
| Compound 477 | 3-DBF | (biphenyl with # and ##) | CA7 | Ph | (biphenyl with ## and #) |
| Compound 478 | 3-DBF | (biphenyl with # and ##) | CA8 | Ph | (biphenyl with ## and #) |
| Compound 479 | 3-DBF | (biphenyl with # and ##) | CA9 | Ph | (biphenyl with ## and #) |
| Compound 480 | 3-DBF | (biphenyl with # and ##) | CA10 | Ph | (biphenyl with ## and #) |
| Compound 510 | 3-DBF | (biphenyl with # and ##) | CA6 | Ph | (methylphenyl with ## and #) |
| Compound 512 | 3-DBF | (biphenyl with # and ##) | CA8 | Ph | (methylphenyl with ## and #) |
| Compound 520 | 3-DBF | (methylphenyl with # and ##) | H | CA1 | (dimethylphenyl with ## and #) |

TABLE 1-continued

| Substituent of compound | Ar | L₁ | R₃ | R₄ | L₂ |
|---|---|---|---|---|---|
| Compound 521 | 3-DBF | (dimethylphenylene, # top, ## bottom) | H | CA2 | (dimethylphenylene, ## top, # bottom) |
| Compound 522 | 3-DBF | (dimethylphenylene, # top, ## bottom) | H | CA3 | (dimethylphenylene, ## top, # bottom) |
| Compound 523 | 3-DBF | (dimethylphenylene, # top, ## bottom) | H | CA4 | (dimethylphenylene, ## top, # bottom) |
| Compound 524 | 3-DBF | (dimethylphenylene, # top, ## bottom) | H | CA5 | (dimethylphenylene, ## top, # bottom) |
| Compound 525 | 3-DBF | (dimethylphenylene, # top, ## bottom) | H | CA6 | (dimethylphenylene, ## top, # bottom) |
| Compound 526 | 3-DBF | (dimethylphenylene, # top, ## bottom) | H | CA7 | (dimethylphenylene, ## top, # bottom) |
| Compound 527 | 3-DBF | (dimethylphenylene, # top, ## bottom) | H | CA8 | (dimethylphenylene, ## top, # bottom) |
| Compound 528 | 3-DBF | (dimethylphenylene, # top, ## bottom) | H | CA9 | (dimethylphenylene, ## top, # bottom) |

TABLE 1-continued
| Substituent of compound | Ar | L₁ | R₃ | R₄ | L₂ |
|---|---|---|---|---|---|
| Compound 529 | 3-DBF | 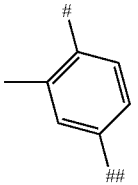 | H | CA10 | 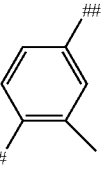 |
| Compound 532 | 3-DBF | 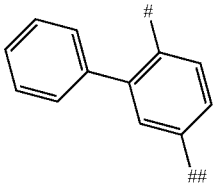 | H | CA1 | 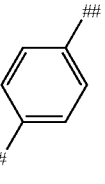 |
| Compound 558 | 3-DBF | 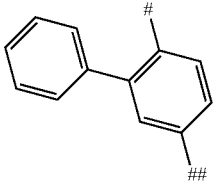 | H | CA2 | 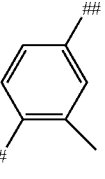 |
| Compound 559 | 3-DBF | 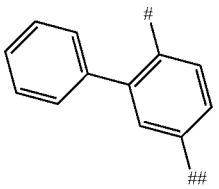 | H | CA3 | 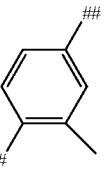 |
| Compound 560 | 3-DBF | 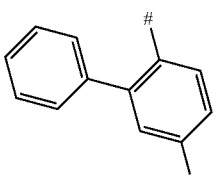 | H | CA4 | 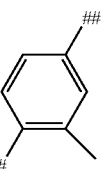 |
| Compound 561 | 3-DBF | 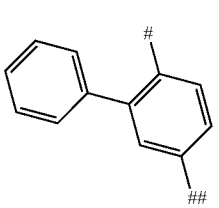 | H | CA5 | 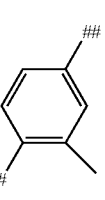 |
| Compound 562 | 3-DBF | 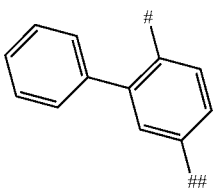 | H | CA6 | 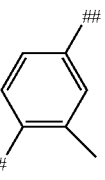 |

TABLE 1-continued

| Substituent of compound | Ar | L₁ | R₃ | R₄ | L₂ |
|---|---|---|---|---|---|
| Compound 563 | 3-DBF | (biphenyl, # at 2-position, ## at 5-position) | H | CA7 | (dimethylphenyl, ## at 1-position, # at 4-position) |
| Compound 564 | 3-DBF | (biphenyl, # at 2-position, ## at 5-position) | H | CA8 | (dimethylphenyl, ## at 1-position, # at 4-position) |
| Compound 565 | 3-DBF | (biphenyl, # at 2-position, ## at 5-position) | H | CA9 | (dimethylphenyl, ## at 1-position, # at 4-position) |
| Compound 566 | 3-DBF | (biphenyl, # at 2-position, ## at 5-position) | H | CA10 | (dimethylphenyl, ## at 1-position, # at 4-position) |
| Compound 569 | 3-DBF | (methylphenyl, # at 1-position, ## at 4-position) | H | CA1 | (biphenyl, ## at 5-position, # at 2-position) |
| Compound 570 | 3-DBF | (methylphenyl, # at 1-position, ## at 4-position) | H | CA2 | (biphenyl, ## at 5-position, # at 2-position) |
| Compound 571 | 3-DBF | (methylphenyl, # at 1-position, ## at 4-position) | H | CA3 | (biphenyl, ## at 5-position, # at 3-position) |

TABLE 1-continued
| Substituent of compound | Ar | L₁ | R₃ | R₄ | L₂ |
|---|---|---|---|---|---|
| Compound 572 | 3-DBF | 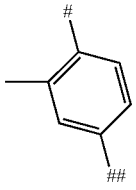 | H | CA4 | 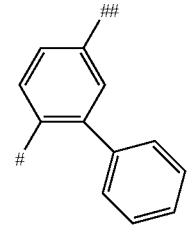 |
| Compound 573 | 3-DBF | 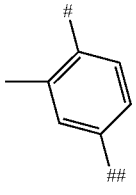 | H | CA5 | 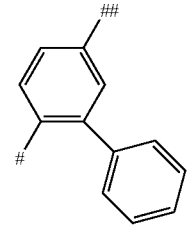 |
| Compound 574 | 3-DBF | 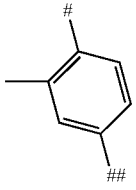 | H | CA6 | 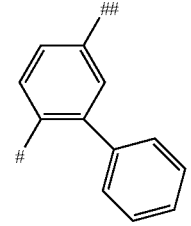 |
| Compound 575 | 3-DBF | 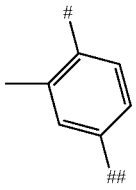 | H | CA7 | 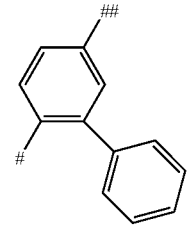 |
| Compound 576 | 3-DBF | 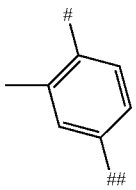 | H | CA8 | 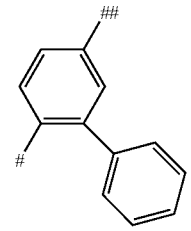 |
| Compound 577 | 3-DBF | 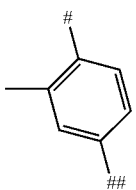 | H | CA9 | 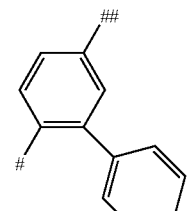 |

TABLE 1-continued

| Substituent of compound | Ar | L₁ | R₃ | R₄ | L₂ |
|---|---|---|---|---|---|
| Compound 578 | 3-DBF | (methylphenylene linker) | H | CA10 | (biphenylene linker) |
| Compound 581 | 3-DBF | (biphenylene linker) | H | CA1 | (biphenylene linker) |
| Compound 582 | 3-DBF | (biphenylene linker) | H | CA2 | (biphenylene linker) |
| Compound 583 | 3-DBF | (biphenylene linker) | H | CA3 | (biphenylene linker) |
| Compound 584 | 3-DBF | (biphenylene linker) | H | CA4 | (biphenylene linker) |
| Compound 585 | 3-DBF | (biphenylene linker) | H | CA5 | (biphenylene linker) |

TABLE 1-continued

| Substituent of compound | Ar | L₁ | R₃ | R₄ | L₂ |
|---|---|---|---|---|---|
| Compound 586 | 3-DBF | [biphenyl structure with # and ##] | H | CA6 | [biphenyl structure with ## and #] |
| Compound 587 | 3-DBF | [biphenyl structure with # and ##] | H | CA8 | [biphenyl structure with ## and #] |
| Compound 588 | 3-DBF | [biphenyl structure with # and ##] | H | CA9 | [biphenyl structure with ## and #] |
| Compound 589 | 3-DBF | [biphenyl structure with # and ##] | H | CA10 | [biphenyl structure with ## and #] |
| Compound 613 | 3-DBF | [biphenyl structure with # and ##] | H | CA1 | [methylphenyl structure with ## and #] |
| Compound 643 | 3-DBF | [biphenyl structure with # and ##] | H | CA7 | [biphenyl structure with ## and #] |
| Compound 725 | 2-DBT | [methylphenyl structure with # and ##] | CA1 | Ph | [methylphenyl structure with ## and #] |

TABLE 1-continued

| Substituent of compound | Ar | L₁ | R₃ | R₄ | L₂ |
|---|---|---|---|---|---|
| Compound 726 | 2-DBT | 2,4-phenylene (#,##) | CA2 | Ph | 3-methyl-1,4-phenylene (##,#) |
| Compound 727 | 2-DBT | 2,4-phenylene (#,##) | CA3 | Ph | 3-methyl-1,4-phenylene (##,#) |
| Compound 728 | 2-DBT | 2,4-phenylene (#,##) | CA4 | Ph | 3-methyl-1,4-phenylene (##,#) |
| Compound 729 | 2-DBT | 2,4-phenylene (#,##) | CA5 | Ph | 3-methyl-1,4-phenylene (##,#) |
| Compound 730 | 2-DBT | 2,4-phenylene (#,##) | CA6 | Ph | 3-methyl-1,4-phenylene (##,#) |
| Compound 731 | 2-DBT | 2,4-phenylene (#,##) | CA7 | Ph | 3-methyl-1,4-phenylene (##,#) |
| Compound 732 | 2-DBT | 2,4-phenylene (#,##) | CA8 | Ph | 3-methyl-1,4-phenylene (##,#) |

TABLE 1-continued

| Substituent of compound | Ar | L₁ | R₃ | R₄ | L₂ |
|---|---|---|---|---|---|
| Compound 736 | 2-DBF | biphenyl (#, ##) | H | CA3 | dimethylphenyl (#, ##) |
| Compound 737 | 2-DBT | methylphenyl (#, ##) | CA9 | Ph | dimethylphenyl (#, ##) |
| Compound 738 | 2-DBT | methylphenyl (#, ##) | CA10 | Ph | dimethylphenyl (#, ##) |
| Compound 782 | 2-DBT | biphenyl (#, ##) | CA1 | Ph | dimethylphenyl (#, ##) |
| Compound 783 | 2-DBT | biphenyl (#, ##) | CA2 | Ph | dimethylphenyl (#, ##) |
| Compound 784 | 2-DBT | biphenyl (#, ##) | CA3 | Ph | dimethylphenyl (#, ##) |
| Compound 785 | 2-DBT | biphenyl (#, ##) | CA4 | Ph | dimethylphenyl (#, ##) |
| Compound 786 | 2-DBT | biphenyl (#, ##) | CA5 | Ph | dimethylphenyl (#, ##) |

TABLE 1-continued

| Substituent of compound | Ar | L₁ | R₃ | R₄ | L₂ |
|---|---|---|---|---|---|
| Compound 787 | 2-DBT | biphenyl (#, ##) | CA6 | Ph | dimethylphenyl (#, ##) |
| Compound 788 | 2-DBT | biphenyl (#, ##) | CA7 | Ph | dimethylphenyl (#, ##) |
| Compound 789 | 2-DBT | biphenyl (#, ##) | CA8 | Ph | dimethylphenyl (#, ##) |
| Compound 790 | 2-DBT | biphenyl (#, ##) | CA9 | Ph | dimethylphenyl (#, ##) |
| Compound 791 | 2-DBT | biphenyl (#, ##) | CA10 | Ph | dimethylphenyl (#, ##) |
| Compound 795 | 2-DBT | methylphenyl (#, ##) | CA1 | Ph | biphenyl (#, ##) |
| Compound 796 | 2-DBT | methylphenyl (#, ##) | CA2 | Ph | biphenyl (#, ##) |

TABLE 1-continued

| Substituent of compound | Ar | L₁ | R₃ | R₄ | L₂ |
|---|---|---|---|---|---|
| Compound 797 | 2-DBT | (structure) | CA3 | Ph | (structure) |
| Compound 798 | 2-DBT | (structure) | CA4 | Ph | (structure) |
| Compound 799 | 2-DBT | (structure) | CA5 | Ph | (structure) |
| Compound 800 | 2-DBT | (structure) | CA6 | Ph | (structure) |
| Compound 801 | 2-DBT | (structure) | CA7 | Ph | (structure) |
| Compound 802 | 2-DBT | (structure) | CA8 | Ph | (structure) |

TABLE 1-continued
| Substituent of compound | Ar | L₁ | R₃ | R₄ | L₂ |
|---|---|---|---|---|---|
| Compound 803 | 2-DBT | 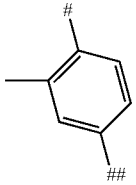 | CA9 | Ph | 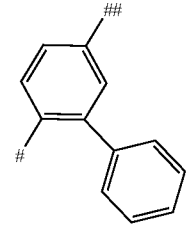 |
| Compound 804 | 2-DBT | 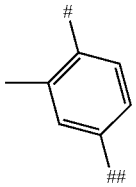 | CA10 | Ph | 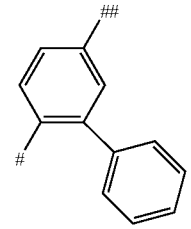 |
| Compound 807 | 2-DBT | 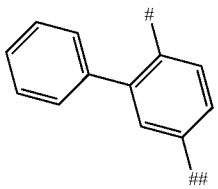 | CA1 | Ph | 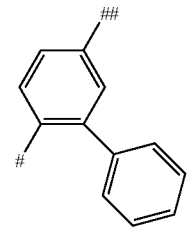 |
| Compound 808 | 2-DBT | 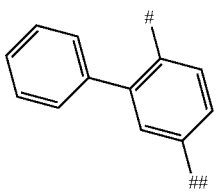 | CA2 | Ph | 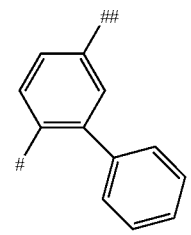 |
| Compound 809 | 2-DBT | 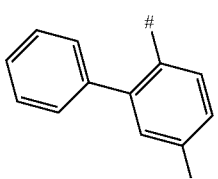 | CA3 | Ph | 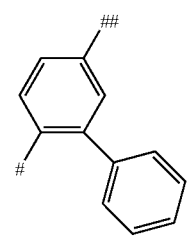 |
| Compound 810 | 2-DBT | 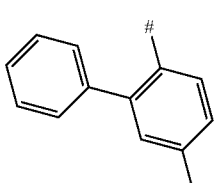 | CA4 | Ph | 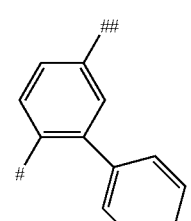 |

TABLE 1-continued

| Substituent of compound | Ar | L₁ | R₃ | R₄ | L₂ |
|---|---|---|---|---|---|
| Compound 811 | 2-DBT | [biphenyl structure with # and ##] | CA5 | Ph | [biphenyl structure with ## and #] |
| Compound 812 | 2-DBT | [biphenyl structure with # and ##] | CA6 | Ph | [biphenyl structure with ## and #] |
| Compound 813 | 2-DBT | [biphenyl structure with # and ##] | CA7 | Ph | [biphenyl structure with ## and #] |
| Compound 814 | 2-DBT | [biphenyl structure with # and ##] | CA8 | Ph | [biphenyl structure with ## and #] |
| Compound 815 | 2-DBT | [biphenyl structure with # and ##] | CA9 | Ph | [biphenyl structure with ## and #] |
| Compound 816 | 2-DBT | [biphenyl structure with # and ##] | CA10 | Ph | [biphenyl structure with ## and #] |

TABLE 1-continued
| Substituent of compound | Ar | L₁ | R₃ | R₄ | L₂ |
|---|---|---|---|---|---|
| Compound 857 | 2-DBT | 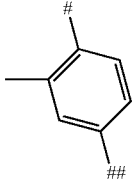 | H | CA1 | 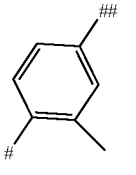 |
| Compound 858 | 2-DBT | 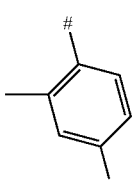 | H | CA2 | 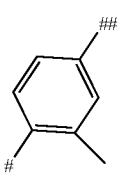 |
| Compound 859 | 2-DBT | 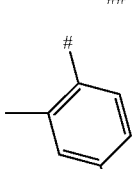 | H | CA3 | 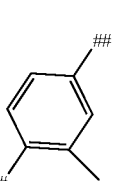 |
| Compound 860 | 2-DBT | 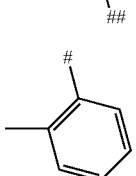 | H | CA4 | 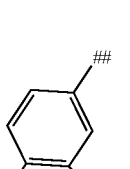 |
| Compound 861 | 2-DBT | 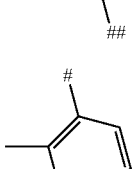 | H | CA5 | 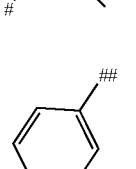 |
| Compound 864 | 2-DBT | 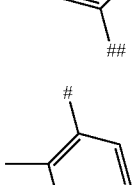 | H | CA6 | 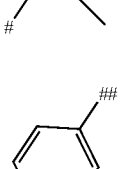 |
| Compound 866 | 2-DBT | 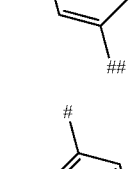 | H | CA7 | 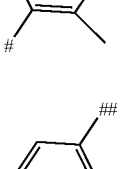 |
| Compound 867 | 2-DBT | 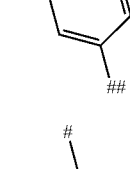 | H | CA8 | 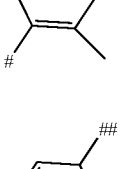 |

TABLE 1-continued

| Substituent of compound | Ar | L₁ | R₃ | R₄ | L₂ |
|---|---|---|---|---|---|
| Compound 868 | 2-DBT | (2,4-disubstituted methylphenyl) | H | CA9 | (2,5-disubstituted methylphenyl) |
| Compound 869 | 2-DBT | (2,4-disubstituted methylphenyl) | H | CA10 | (2,5-disubstituted methylphenyl) |
| Compound 881 | 3-DBF | (2,4-disubstituted methylphenyl) | CA4 | Ph | (2,5-disubstituted methylphenyl) |
| Compound 882 | 3-DBF | (2,4-disubstituted methylphenyl) | CA5 | Ph | (2,5-disubstituted methylphenyl) |
| Compound 901 | 2-DBT | (2,5-disubstituted biphenyl) | H | CA1 | (2,5-disubstituted methylphenyl) |
| Compound 902 | 2-DBT | (2,5-disubstituted biphenyl) | H | CA2 | (2,5-disubstituted methylphenyl) |
| Compound 903 | 2-DBT | (2,5-disubstituted biphenyl) | H | CA3 | (2,5-disubstituted methylphenyl) |

TABLE 1-continued

| Substituent of compound | Ar | L₁ | R₃ | R₄ | L₂ |
|---|---|---|---|---|---|
| Compound 904 | 2-DBT | (biphenyl group) | H | CA4 | (dimethylphenyl group) |
| Compound 905 | 2-DBT | (biphenyl group) | H | CA5 | (dimethylphenyl group) |
| Compound 906 | 2-DBT | (biphenyl group) | H | CA6 | (dimethylphenyl group) |
| Compound 907 | 2-DBT | (biphenyl group) | H | CA7 | (dimethylphenyl group) |
| Compound 908 | 2-DBT | (biphenyl group) | H | CA8 | (dimethylphenyl group) |
| Compound 909 | 2-DBT | (biphenyl group) | H | CA10 | (dimethylphenyl group) |
| Compound 912 | 2-DBT | (methylphenyl group) | H | CA1 | (phenyl-substituted phenyl group) |

TABLE 1-continued

| Substituent of compound | Ar | L₁ | R₃ | R₄ | L₂ |
|---|---|---|---|---|---|
| Compound 913 | 2-DBT | (2,4-phenylene, # at 1, ## at 4) | H | CA2 | (biphenyl-3,5-diyl, ## at 3, # at 5) |
| Compound 914 | 2-DBT | (2,4-phenylene, # at 1, ## at 4) | H | CA3 | (biphenyl-3,5-diyl, ## at 3, # at 5) |
| Compound 915 | 2-DBT | (2,4-phenylene, # at 1, ## at 4) | H | CA4 | (biphenyl-3,5-diyl, ## at 3, # at 5) |
| Compound 916 | 2-DBT | (2,4-phenylene, # at 1, ## at 4) | H | CA5 | (biphenyl-3,5-diyl, ## at 3, # at 5) |
| Compound 917 | 2-DBT | (2,4-phenylene, # at 1, ## at 4) | H | CA6 | (biphenyl-3,5-diyl, ## at 3, # at 5) |
| Compound 918 | 2-DBT | (2,4-phenylene, # at 1, ## at 4) | H | CA7 | (biphenyl-3,5-diyl, ## at 3, # at 5) |

TABLE 1-continued

| Substituent of compound | Ar | L₁ | R₃ | R₄ | L₂ |
|---|---|---|---|---|---|
| Compound 919 | 2-DBT | (2-methyl-1,4-phenylene) | H | CA8 | (biphenyl-diyl) |
| Compound 920 | 2-DBT | (2-methyl-1,4-phenylene) | H | CA9 | (biphenyl-diyl) |
| Compound 921 | 2-DBT | (2-methyl-1,4-phenylene) | H | CA10 | (biphenyl-diyl) |
| Compound 924 | 2-DBT | (biphenyl-diyl) | H | CA1 | (biphenyl-diyl) |
| Compound 925 | 2-DBT | (biphenyl-diyl) | H | CA2 | (biphenyl-diyl) |
| Compound 927 | 2-DBT | (biphenyl-diyl) | H | CA3 | (biphenyl-diyl) |

TABLE 1-continued

| Substituent of compound | Ar | L₁ | R₃ | R₄ | L₂ |
|---|---|---|---|---|---|
| Compound 928 | 2-DBT | (biphenyl with # and ##) | H | CA4 | (biphenyl with ## and #) |
| Compound 929 | 2-DBT | (biphenyl with # and ##) | H | CA5 | (biphenyl with ## and #) |
| Compound 930 | 2-DBT | (biphenyl with # and ##) | H | CA6 | (biphenyl with ## and #) |
| Compound 931 | 2-DBT | (biphenyl with # and ##) | H | CA7 | (biphenyl with ## and #) |
| Compound 932 | 2-DBT | (biphenyl with # and ##) | H | CA8 | (biphenyl with ## and #) |
| Compound 933 | 2-DBT | (biphenyl with # and ##) | H | CA9 | (biphenyl with ## and #) |

TABLE 1-continued

| Substituent of compound | Ar | L₁ | R₃ | R₄ | L₂ |
|---|---|---|---|---|---|
| Compound 934 | 2-DBT | (biphenyl, # upper, ## lower) | H | CA10 | (biphenyl, ## upper, # lower) |
| Compound 937 | 3-DBF | (methylphenyl, # upper, ## lower) | CA6 | Ph | (biphenyl, ## upper, # lower) |
| Compound 938 | 3-DBF | (methylphenyl, # upper, ## lower) | CA7 | Ph | (biphenyl, ## upper, # lower) |
| Compound 941 | 2-DBF | (biphenyl, # upper, ## lower) | H | CA1 | (dimethylphenyl, ## upper, # lower) |
| Compound 942 | 2-DBF | (biphenyl, # upper, ## lower) | H | CA2 | (dimethylphenyl, ## upper, # lower) |
| Compound 945 | 2-DBT | (biphenyl, # upper, ## lower) | H | CA9 | (dimethylphenyl, ## upper, # lower) |
| Compound 995 | 2-DBF | (methylphenyl, # upper, ## lower) | H | CA10 | (dimethylphenyl, ## upper, # lower) |

TABLE 1-continued
| Substituent of compound | Ar | L₁ | R₃ | R₄ | L₂ |
|---|---|---|---|---|---|
| Compound 1027 | 3-DBT | 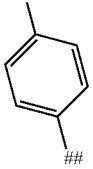 | CA8 | Ph | 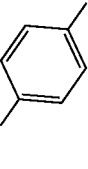 |
| Compound 1047 | 2-DBF | 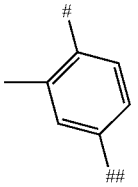 | CA7 | Ph | 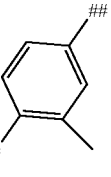 |
| Compound 1048 | 2-DBF | 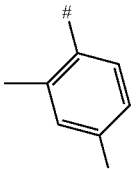 | CA8 | Ph | 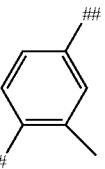 |
| Compound 1083 | 2-DBF | 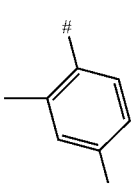 | CA10 | Ph | 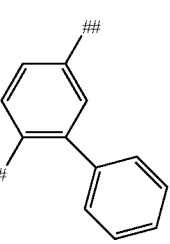 |
| Compound 1086 | 3-DBT | 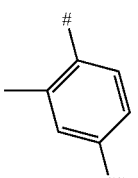 | CA1 | Ph | 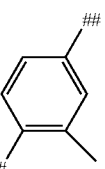 |
| Compound 1088 | 3-DBT | 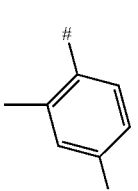 | CA2 | Ph | 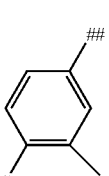 |
| Compound 1089 | 3-DBT | 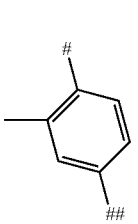 | CA3 | Ph | 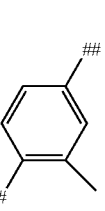 |

TABLE 1-continued

| Substituent of compound | Ar | L₁ | R₃ | R₄ | L₂ |
|---|---|---|---|---|---|
| Compound 1090 | 3-DBT | (3-methylphenylene, # top, ## bottom) | CA4 | Ph | (3-methylphenylene, ## top, # bottom) |
| Compound 1091 | 3-DBT | (3-methylphenylene, # top, ## bottom) | CA5 | Ph | (3-methylphenylene, ## top, # bottom) |
| Compound 1092 | 3-DBT | (3-methylphenylene, # top, ## bottom) | CA6 | Ph | (3-methylphenylene, ## top, # bottom) |
| Compound 1093 | 3-DBT | (3-methylphenylene, # top, ## bottom) | CA7 | Ph | (3-methylphenylene, ## top, # bottom) |
| Compound 1094 | 3-DBT | (3-methylphenylene, # top, ## bottom) | CA8 | Ph | (3-methylphenylene, ## top, # bottom) |
| Compound 1095 | 3-DBT | (3-methylphenylene, # top, ## bottom) | CA9 | Ph | (3-methylphenylene, ## top, # bottom) |
| Compound 1096 | 3-DBT | (3-methylphenylene, # top, ## bottom) | CA10 | Ph | (3-methylphenylene, ## top, # bottom) |
| Compound 1137 | 3-DBT | (biphenylene, # top, ## bottom) | CA1 | Ph | (3-methylphenylene, ## top, # bottom) |

TABLE 1-continued

| Substituent of compound | Ar | L₁ | R₃ | R₄ | L₂ |
|---|---|---|---|---|---|
| Compound 1138 | 3-DBT | biphenyl | CA2 | Ph | dimethylphenyl |
| Compound 1139 | 3-DBT | biphenyl | CA3 | Ph | dimethylphenyl |
| Compound 1140 | 3-DBT | biphenyl | CA4 | Ph | dimethylphenyl |
| Compound 1141 | 3-DBT | biphenyl | CA5 | Ph | dimethylphenyl |
| Compound 1142 | 3-DBT | biphenyl | CA6 | Ph | dimethylphenyl |
| Compound 1143 | 3-DBT | biphenyl | CA7 | Ph | dimethylphenyl |
| Compound 1144 | 3-DBT | biphenyl | CA8 | Ph | dimethylphenyl |

TABLE 1-continued

| Substituent of compound | Ar | L₁ | R₃ | R₄ | L₂ |
|---|---|---|---|---|---|
| Compound 1145 | 3-DBT | (biphenyl linker) | CA9 | Ph | (methylphenyl linker) |
| Compound 1146 | 3-DBT | (biphenyl linker) | CA10 | Ph | (methylphenyl linker) |
| Compound 1149 | 3-DBT | (methylphenyl linker) | CA1 | Ph | (biphenyl linker) |
| Compound 1150 | 3-DBT | (methylphenyl linker) | CA2 | Ph | (biphenyl linker) |
| Compound 1151 | 3-DBT | (methylphenyl linker) | CA3 | Ph | (biphenyl linker) |
| Compound 1153 | 3-DBT | (methylphenyl linker) | CA4 | Ph | (biphenyl linker) |
| Compound 1154 | 3-DBT | (methylphenyl linker) | CA5 | Ph | (biphenyl linker) |

TABLE 1-continued

| Substituent of compound | Ar | L₁ | R₃ | R₄ | L₂ |
|---|---|---|---|---|---|
| Compound 1155 | 3-DBT | [structure] | CA6 | Ph | [structure] |
| Compound 1156 | 3-DBT | [structure] | CA7 | Ph | [structure] |
| Compound 1157 | 3-DBT | [structure] | CA8 | Ph | [structure] |
| Compound 1158 | 3-DBT | [structure] | CA9 | Ph | [structure] |
| Compound 1159 | 3-DBT | [structure] | CA10 | Ph | [structure] |
| Compound 1162 | 3-DBT | [structure] | CA1 | Ph | [structure] |

TABLE 1-continued

| Substituent of compound | Ar | L₁ | R₃ | R₄ | L₂ |
|---|---|---|---|---|---|
| Compound 1163 | 3-DBT | (biphenyl with # and ##) | CA2 | Ph | (biphenyl with ## and #) |
| Compound 1166 | 3-DBT | (biphenyl with # and ##) | CA3 | Ph | (biphenyl with ## and #) |
| Compound 1167 | 3-DBT | (biphenyl with # and ##) | CA4 | Ph | (biphenyl with ## and #) |
| Compound 1168 | 3-DBT | (biphenyl with # and ##) | CA5 | Ph | (biphenyl with ## and #) |
| Compound 1169 | 3-DBT | (biphenyl with # and ##) | CA6 | Ph | (biphenyl with ## and #) |
| Compound 1170 | 3-DBT | (biphenyl with # and ##) | CA7 | Ph | (biphenyl with ## and #) |

TABLE 1-continued

| Substituent of compound | Ar | L₁ | R₃ | R₄ | L₂ |
|---|---|---|---|---|---|
| Compound 1171 | 3-DBT | (biphenyl) | CA8 | Ph | (biphenyl) |
| Compound 1172 | 3-DBT | (biphenyl) | CA9 | Ph | (biphenyl) |
| Compound 1173 | 3-DBT | (biphenyl) | CA10 | Ph | (biphenyl) |
| Compound 1189 | 3-DBT | (methylphenyl) | H | CA1 | (phenyl) |
| Compound 1218 | 3-DBT | (methylphenyl) | H | CA1 | (methylphenyl) |
| Compound 1219 | 3-DBT | (methylphenyl) | H | CA2 | (methylphenyl) |
| Compound 1220 | 3-DBT | (methylphenyl) | H | CA3 | (methylphenyl) |

TABLE 1-continued
| Substituent of compound | Ar | L₁ | R₃ | R₄ | L₂ |
|---|---|---|---|---|---|
| Compound 1221 | 3-DBT | 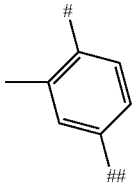 | H | CA4 | 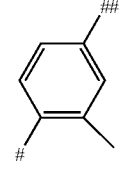 |
| Compound 1222 | 3-DBT | 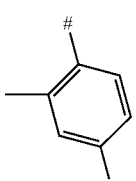 | H | CA5 | 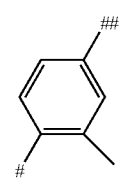 |
| Compound 1223 | 3-DBT | 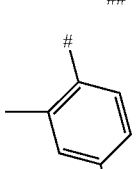 | H | CA6 | 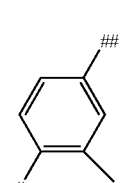 |
| Compound 1224 | 3-DBT | 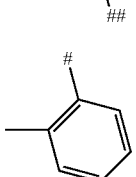 | H | CA7 | 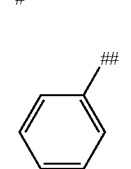 |
| Compound 1227 | 3-DBT | 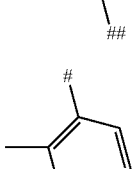 | H | CA8 | 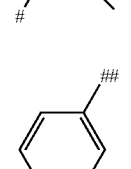 |
| Compound 1228 | 3-DBT | 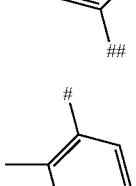 | H | CA9 | 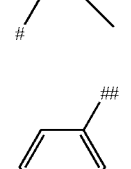 |
| Compound 1229 | 3-DBT |  | H | CA10 | 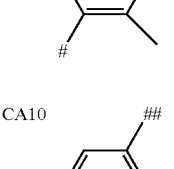 |
| Compound 1258 | 3-DBT | 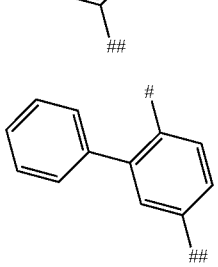 | H | CA1 | 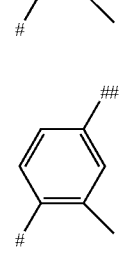 |

TABLE 1-continued

| Substituent of compound | Ar | L₁ | R₃ | R₄ | L₂ |
|---|---|---|---|---|---|
| Compound 1259 | 3-DBT | biphenyl | H | CA2 | dimethylphenyl |
| Compound 1260 | 3-DBT | biphenyl | H | CA3 | dimethylphenyl |
| Compound 1261 | 3-DBT | biphenyl | H | CA4 | dimethylphenyl |
| Compound 1262 | 3-DBT | biphenyl | H | CA5 | dimethylphenyl |
| Compound 1263 | 3-DBT | biphenyl | H | CA6 | dimethylphenyl |
| Compound 1264 | 3-DBT | biphenyl | H | CA7 | dimethylphenyl |
| Compound 1265 | 3-DBT | biphenyl | H | CA8 | dimethylphenyl |
| Compound 1266 | 3-DBT | biphenyl | H | CA9 | dimethylphenyl |

TABLE 1-continued

| Substituent of compound | Ar | L₁ | R₃ | R₄ | L₂ |
|---|---|---|---|---|---|
| Compound 1267 | 3-DBT | (biphenyl group with # and ##) | H | CA10 | (dimethylphenyl group with ## and #) |
| Compound 1270 | 3-DBT | (methylphenyl group with # and ##) | H | CA1 | (biphenyl group with ## and #) |
| Compound 1271 | 3-DBT | (methylphenyl group with # and ##) | H | CA2 | (biphenyl group with ## and #) |
| Compound 1273 | 3-DBT | (methylphenyl group with # and ##) | H | CA3 | (biphenyl group with ## and #) |
| Compound 1274 | 3-DBT | (methylphenyl group with # and ##) | H | CA4 | (biphenyl group with ## and #) |
| Compound 1275 | 3-DBT | (methylphenyl group with # and ##) | H | CA5 | (biphenyl group with ## and #) |

TABLE 1-continued

| Substituent of compound | Ar | L₁ | R₃ | R₄ | L₂ |
|---|---|---|---|---|---|
| Compound 1276 | 3-DBT | (2,4-phenylene, # at 1, ## at 4, methyl at 3) | H | CA6 | (biphenyl-3,5-diyl, ## at 5, # at 3, phenyl at 2) |
| Compound 1277 | 3-DBT | (2,4-phenylene, # at 1, ## at 4, methyl at 3) | H | CA7 | (biphenyl-3,5-diyl, ## at 5, # at 3, phenyl at 2) |
| Compound 1278 | 3-DBT | (2,4-phenylene, # at 1, ## at 4, methyl at 3) | H | CA8 | (biphenyl-3,5-diyl, ## at 5, # at 3, phenyl at 2) |
| Compound 1279 | 3-DBT | (2,4-phenylene, # at 1, ## at 4, methyl at 3) | H | CA9 | (biphenyl-3,5-diyl, ## at 5, # at 3, phenyl at 2) |
| Compound 1280 | 3-DBT | (2,4-phenylene, # at 1, ## at 4, methyl at 3) | H | CA10 | (biphenyl-3,5-diyl, ## at 5, # at 3, phenyl at 2) |
| Compound 1283 | 3-DBT | (biphenyl-2,4-diyl, # at 1, ## at 4, phenyl at 2) | H | CA1 | (biphenyl-3,5-diyl, ## at 5, # at 3, phenyl at 2) |

TABLE 1-continued

| Substituent of compound | Ar | L₁ | R₃ | R₄ | L₂ |
|---|---|---|---|---|---|
| Compound 1284 | 3-DBT | (biphenyl, # top, ## bottom) | H | CA2 | (biphenyl, ## top, # bottom) |
| Compound 1285 | 3-DBT | (biphenyl, # top, ## bottom) | H | CA3 | (biphenyl, ## top, # bottom) |
| Compound 1286 | 3-DBT | (biphenyl, # top, ## bottom) | H | CA4 | (biphenyl, ## top, # bottom) |
| Compound 1287 | 3-DBT | (biphenyl, # top, ## bottom) | H | CA5 | (biphenyl, ## top, # bottom) |
| Compound 1288 | 3-DBT | (biphenyl, # top, ## bottom) | H | CA6 | (biphenyl, ## top, # bottom) |
| Compound 1289 | 3-DBT | (biphenyl, # top, ## bottom) | H | CA7 | (biphenyl, ## top, # bottom) |

TABLE 1-continued

| Substituent of compound | Ar | L₁ | R₃ | R₄ | L₂ |
|---|---|---|---|---|---|
| Compound 1290 | 3-DBT | (biphenyl structure with # and ##) | H | CA8 | (biphenyl structure with ## and #) |
| Compound 1291 | 3-DBT | (biphenyl structure with # and ##) | H | CA9 | (biphenyl structure with ## and #) |
| Compound 1294 | 3-DBT | (biphenyl structure with # and ##) | H | CA10 | (biphenyl structure with ## and #) |

For example, according to Table 1, in Compound 1294, Ar is 3-DBT, L₁ is

L₂

R₃ is H, and R₄ is CA10. The structural formula of Compound 1294 is:

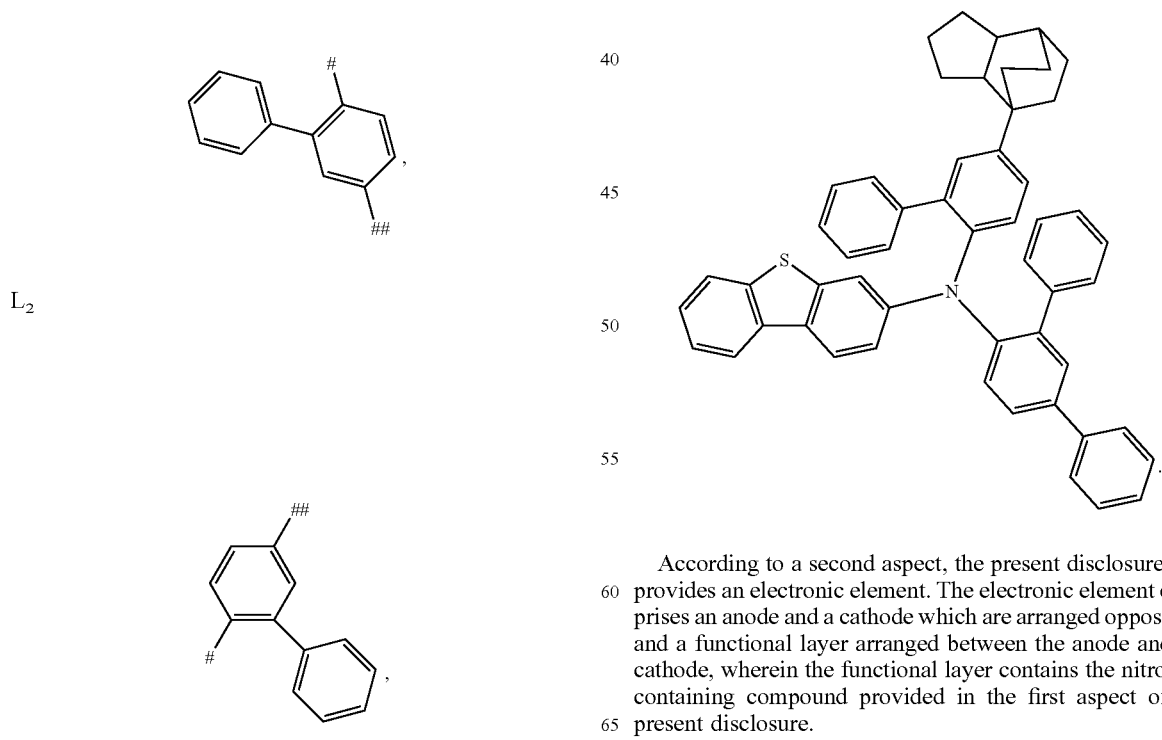

According to a second aspect, the present disclosure also provides an electronic element. The electronic element comprises an anode and a cathode which are arranged oppositely, and a functional layer arranged between the anode and the cathode, wherein the functional layer contains the nitrogen-containing compound provided in the first aspect of the present disclosure.

The nitrogen-containing compound provided by the present disclosure may be used to form at least one organic membrane layer of the functional layer so as to improve the voltage characteristic, efficiency characteristic and life characteristic of the electronic element.

Optionally, the organic membrane layer containing the nitrogen-containing compound of the present disclosure is located between the anode and the energy conversion layer of the electronic element, so that hole transport between the anode and the energy conversion layer is improved.

Optionally, the functional layer includes a hole transporting layer, and the hole transporting layer contains the nitrogen-containing compound provided by the present disclosure. Where the hole transporting layer may consist of the nitrogen-containing compound provided by the present disclosure, and may also consist of the nitrogen-containing compound provided by the present disclosure and other materials jointly.

According to one embodiment, the hole transporting layer includes a first hole transporting layer and a second hole transporting layer, and the first hole transporting layer is arranged closer to the surface of the anode relative to the second hole transporting layer. The first hole transporting layer and/or the second hole transporting layer contains the nitrogen-containing compound provided by the present disclosure. In other words, one layer of the first hole transporting layer and the second hole transporting layer may contain the nitrogen-containing compound provided by the present disclosure, or both the first hole transporting layer and the second hole transporting layer may contain the nitrogen-containing compound provided by the present disclosure. It may be understood that the first hole transporting layer and the second hole transporting layer may also contain other materials, or may also not contain other materials. Optionally, the second hole transporting layer consists of the nitrogen-containing compound.

According to one preferred embodiment, as shown in FIG. 1, the electronic element is an organic electroluminescent device. The organic electroluminescent device includes an anode 100, a first hole transporting layer 321, a second hole transporting layer 322, an organic light-emitting layer 330 serving as the energy conversion layer, an electron transporting layer 340 and a cathode 200 which are sequentially stacked. The nitrogen-containing compound provided by the present disclosure may be applied to the second hole transporting layer 322 of the organic electroluminescent device, so as to prolong the life of the organic electroluminescent device, improve the luminous efficiency of the organic electroluminescent device and reduce the driving voltage of the organic electroluminescent device.

In the present disclosure, the anode 100 includes an anode material, preferably a material with a large work function and facilitating hole injection into the functional layer. The specific examples of the anode material include, but are not limited to, metals such as nickel, platinum, vanadium, chromium, copper, zinc and gold or alloys thereof, metal oxides such as zinc oxide, indium tin oxide (ITO) and indium zinc oxide (IZO); combination of metals and oxides such as ZnO:Al or $SnO_2$:Sb; or conductive polymers such as poly(3-methylthiophene), poly[3,4-(ethylene-1,2-dioxy)thiophene] (PEDT), polypyrrole and polyaniline. A transparent electrode containing indium tin oxide (ITO) as an anode is preferably included.

Optionally, the first hole transporting layer 321 includes one or more hole transporting materials. The hole transporting material may be selected from a carbazole polymer, a carbazole linked triarylamine compound or other types of compounds, which is not particularly limited in the present disclosure. For example, the first hole transporting layer 321 may consist of compound NPB.

Optionally, the organic light-emitting layer 330 is composed of a single light-emitting material, or also contains a host material and a guest material. In one specific embodiment, the organic light-emitting layer 330 consists of a host material and a guest material. Holes injected into the organic light-emitting layer 330 and electrons injected into the organic light-emitting layer 330 may be combined in the organic light-emitting layer 330 to form excitons, the excitons transfer energy to the host material, and the host material transfers energy to the guest material, so that the guest material can emit light.

The host material of the organic light-emitting layer 330 may be a metal-chelated compound, a bisstyryl derivative, an aromatic amine derivative, a dibenzofuran derivative, or other types of materials, which is not particularly limited in the present disclosure. In one embodiment of the present disclosure, the host material of the organic light-emitting layer 330 may be CBP.

The guest material of the organic light-emitting layer 330 may be a compound with a condensed aryl ring or a derivative thereof, a compound with heteroaryl ring or a derivative thereof, and an aromatic amine derivative or other materials, which is not particularly limited in the present disclosure. In one embodiment of the present disclosure, the guest material of the organic light-emitting layer 330 may be green phosphorescent material, and may be, for example, $Ir(ppy)_3$ and the like.

The electron transporting layer 340 may be of a single-layer structure, or may also be of a multi-layer structure, which may include one or more electron transporting materials. The electron transporting materials may be selected from, but is not limited to, benzimidazole derivatives, oxadiazole derivatives, quinoxaline derivatives or other electron transporting materials. In one embodiment of the present disclosure, the electron transporting layer 340 may consist of DBimiBphen and LiQ.

In the present disclosure, the cathode 200 includes a cathode material, which is a material with a small work function and facilitating electron injection into the functional layer. The specific examples of the cathode material include, but are not limited to, metals such as magnesium, calcium, sodium, potassium, titanium, indium, yttrium, lithium, gadolinium, aluminum, silver, tin and lead or alloys thereof; or multi-layer materials such as LiF/Al, Liq/Al, $LiO_2$/Al, LiF/Ca, LiF/Al and $BaF_2$/Ca. A metal electrode containing aluminum as a cathode is preferably included.

Optionally, as shown in FIG. 1, a hole injecting layer 310 is also be provided between the anode 100 and the first hole transporting layer 321, so as to enhance the capability of injecting holes into the first hole transporting layer 321. The hole injecting layer 310 may choose benzidine derivatives, starburst arylamine compounds, phthalocyanine derivatives or other materials, which is not particularly limited in the present disclosure. For example, the hole injecting layer 310 may consist of m-MTDATA.

Optionally, as shown in FIG. 1, an electron injecting layer 350 is also be provided between the cathode 200 and the electron transporting layer 340, so as to enhance the capability of injecting electrons into the electron transporting layer 340. The electron injection layer 350 may include inorganic materials such as alkali metal sulfide and alkali metal halide, or may include complexes of alkali metal and organic matter. For example, the electron injecting layer 350 may include LiQ.

Figure 3:
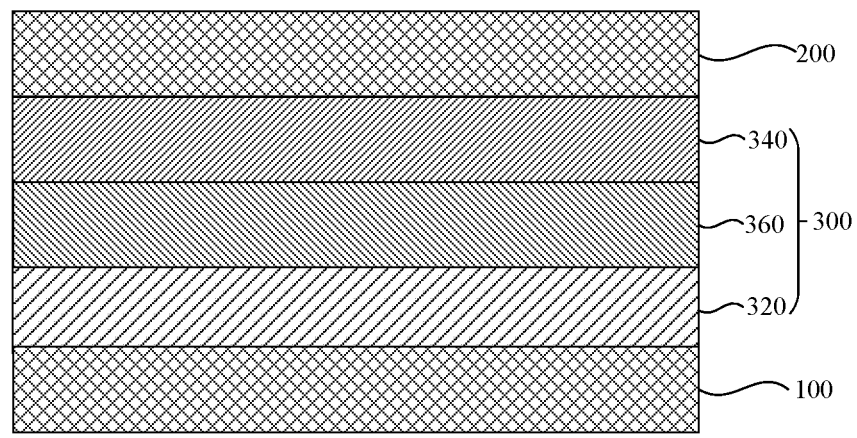
FIG. 3 is a structural schematic diagram of a photoelectric conversion device according to the embodiments of the present disclosure.

According to another preferred embodiment, the electronic element is a photoelectric conversion device. As shown in FIG. 3, the photoelectric conversion device includes an anode 100 and a cathode 200 which are arranged oppositely, and a functional layer 300 arranged between the anode 100 and the cathode 200, wherein the functional layer 300 contains the nitrogen-containing compound provided by the present disclosure.

According to one embodiment, as shown in FIG. 3, the functional layer 300 includes a hole transporting layer 320, and the hole transporting layer 320 contains the nitrogen-containing compound provided by the present disclosure. The hole transporting layer 320 may consist of the nitrogen-containing compound provided by the present disclosure, and may also consist of the nitrogen-containing compound provided by the present disclosure and other materials jointly.

Optionally, the hole transporting layer 320 also includes inorganic doped materials, so that the hole transporting performance of the hole transporting layer 320 can be improved.

According to one specific embodiment, as shown in FIG. 3, the photoelectric conversion device includes an anode 100, a hole transporting layer 320, a photoelectric conversion layer 360, an electron transporting layer 340 and a cathode 200 which are sequentially stacked.

Optionally, the photoelectric conversion device is a solar battery, and particularly is an organic thin film solar battery. For example, in one embodiment of the present disclosure, the solar battery includes an anode, a hole transporting layer, a photoelectric conversion layer, an electron transporting layer and a cathode which are sequentially stacked, where the hole transporting layer contains the nitrogen-containing compound provided by the present disclosure.

According to a third aspect of the present disclosure, the embodiments of the present disclosure also provide an electronic apparatus. The electronic apparatus includes any one electronic element described by the embodiments of the electronic element provided in the second aspect of the present disclosure. The electronic apparatus has any one electronic element described by the embodiments of the electronic element, so the electronic apparatus has the same beneficial effects, which will not be elaborated here.

Figure 2:
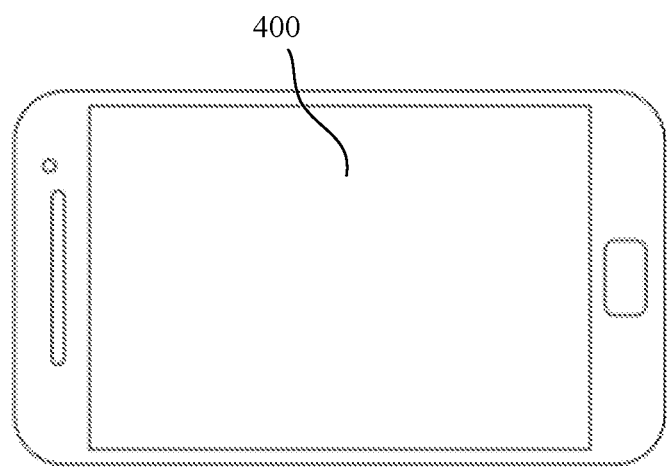
FIG. 2 is a structural schematic diagram of an electronic apparatus according to the embodiments of the present disclosure.

For example, as shown in FIG. 2, the present disclosure provides an electronic apparatus 400. The electronic apparatus 400 includes any one organic electroluminescent device described by the above embodiments of the organic electroluminescent device. The electronic apparatus 400 may be a display apparatus, a lighting apparatus, an optical communication apparatus, or other types of electronic apparatus. For example, the electronic apparatus 400 may include, but is not limited to, a computer screen, a mobile phone screen, a television, an electronic paper, an emergency lighting, and an optical module, etc. The electronic apparatus 400 has any one organic electroluminescent device described by the above embodiments of the organic electroluminescent device, so the electronic apparatus 400 has the same beneficial effects, which will not be elaborated here.

Figure 4:
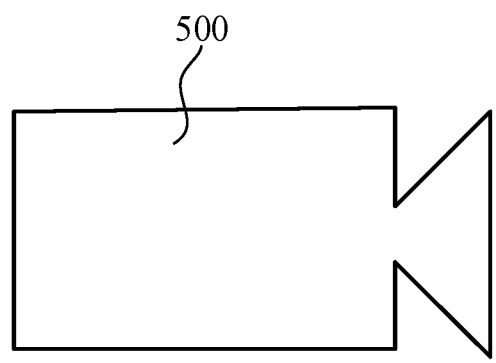
FIG. 4 is a structural schematic diagram of an electronic apparatus according to the embodiments of the present disclosure.

For another example, as shown in FIG. 4, the present disclosure provides an electronic apparatus 500. The electronic apparatus 500 includes any one photoelectric conversion device described by the above embodiments of the photoelectric conversion device. The electronic apparatus 500 may be a solar power generation equipment, a photo-detector, a fingerprint identification equipment, an optical module, a CCD camera, or other types of electronic apparatus. The electronic apparatus 500 has any one photoelectric conversion device described by the above embodiments of the photoelectric conversion device, so the electronic apparatus 500 has the same beneficial effects, which will not be elaborated here.

Hereinafter, the present disclosure is further described in detail through the examples. However, the following examples are only illustration of the present disclosure, and does not limit the present disclosure.

The following synthesis examples 1 to 22 are used to describe the compounds and the preparation method thereof.

Synthesis Example 1

Figure 6:
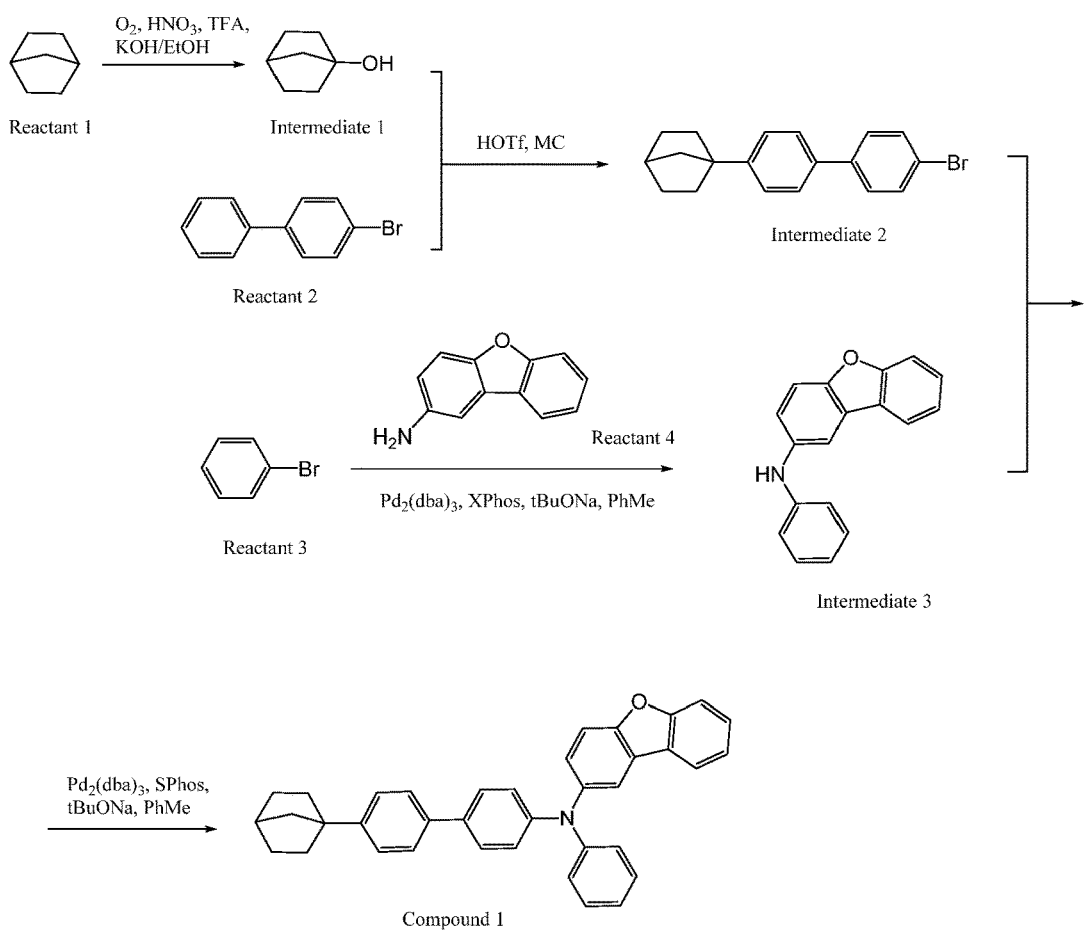
FIG. 6 shows the synthetic route of Compound 1.

According to the synthetic route shown in FIG. 6, Compound 1 was synthesized:

Reactant 1 (50.0 g, 520 mmol) and trifluoroacetic acid (TFA) (400 mL) were added into a 1 L round-bottom flask, concentrated nitric acid (1.5 g) was added under a stirring condition, the temperature was raised to 45-50° C., and the mixture was stirred for 16 hours in an air atmosphere; trifluoroacetic acid was removed under reduced pressure, an ethanol solution (500 mL) of 10 wt % potassium hydroxide was added into the remaining mixture, and stirring was performed for 3 hours; ethanol was removed under reduced pressure, methylene chloride was added into the flask, the organic phase was washed with water twice, then dried over anhydrous magnesium sulfate, and the solvent in the organic phase was removed under reduced pressure to obtain a crude product; and the obtained crude product was purified through silica gel column chromatography by using methylene chloride/normal heptane as an eluent to obtain a white powdered intermediate 1 (19.4 g, a yield of 33%).

The intermediate 1 (19.0 g, 169 mmol), reactant 2 (39.5 g, 169 mmol) and methylene chloride (MC) (250 mL) were added into a 500 mL round-bottom flask, and trifluoromethanesulfonic acid (HOTf) (38.1 g, 254 mmol) was added dropwise at −15 to −20° C. under the protection of nitrogen; after dropwise adding, low-temperature stirring was maintained for 8 hours, then the temperature was raised to room temperature (25° C.), and a 10 wt % sodium hydroxide aqueous solution was added into the reaction liquid slowly and dropwise to be neutral; an organic phase was separated and was washed with water twice, the organic phase was dried over anhydrous magnesium sulfate, and the solvent in the organic phase was removed under reduced pressure to obtain a crude product; and the obtained crude product was purified through silica gel column chromatography by using normal heptane as an eluent to obtain a white solid intermediate 2 (34.4 g, a yield of 62%).

Reactant 3 (10.0 g, 64 mmol), reactant 4 (2-aminodibenzofuran) (12.8 g, 70 mmol), tris(dibenzylideneacetone)dipalladium (Pd$_2$(dba)$_3$) (0.6 g, 0.6 mmol), 2-dicyclohexylphosphino-2',4',6'-triisopropylbiphenyl (XPhos) (0.6 g, 1.3 mmol) and sodium tert-butoxide (tBuONa) (9.2 g, 96 mmol) were added into methylbenzene (150 mL), and the mixture was heated to 105-110° C. under the protection of nitrogen and stirred for 1 hour; then the mixture was cooled to room temperature, and reaction liquid was washed with water twice, dried by adding magnesium sulfate, and filtered, the obtained filtrate was allowed to pass through a short silica gel column, and then the liquid passing through the column was decompressed to remove the solvent to obtain a crude product; and the obtained crude product was purified by recrystallization with a methylene dichloride/ethanol system to obtain a light brown solid intermediate 3 (13.2 g, a yield of 80%).

The intermediate 2 (4.0 g, 12.2 mmol), the intermediate 3 (3.2 g, 12.2 mmol), tris(dibenzylideneacetone)dipalladium (0.1 g, 0.1 mmol), 2-dicyclohexylphosphino-2',6'-dimethoxybiphenyl (SPhos) (0.1 g, 0.2 mmol) and sodium tert-butoxide (1.8 g, 18.3 mmol) were added into methylbenzene (40 mL), and the mixture was heated to 105-110° C. under the protection of nitrogen and stirred for 16 hours; then the mixture was cooled to room temperature, reaction liquid was washed with water, dried by adding magnesium sulfate, and filtered, the obtained filtrate was allowed to pass through a short silica gel column, and then the liquid passing through the column was decompressed to remove the solvent to obtain a crude product; and the obtained crude product was purified by recrystallization with a methylene dichloride/normal heptane system to obtain a white solid Compound 1 (2.3 g, a yield of 37%). Mass spectrum: m/z=506.2[M+H]$^+$.

Synthesis Examples 2 to 22

Referring to the method of Compound 1, the compounds listed in Table 2 were synthesized respectively in the synthesis examples 2 to 22, except that the reactant 1 was replaced with reactant A, the reactant 2 was replaced with reactant B, the reactant 3 was replaced with reactant C, and the reactant 4 was replaced with reactant D, where the structural formulas of the reactants and the corresponding compounds, and the yield, the final yield and mass spectrum characterization result of the compounds are shown in Table 2.

TABLE 2
Structure, raw material, yield and mass spectrum characterization of various compounds
| Compound Number | Reactant A | Reactant B | Reactant C | Reactant D | Compound structure | Yield (%) | m/z [M + H]+ |
|---|---|---|---|---|---|---|---|
| Compound 51 | 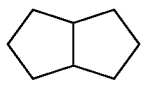 | 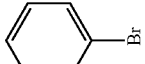 | 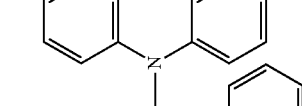 | 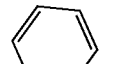 | 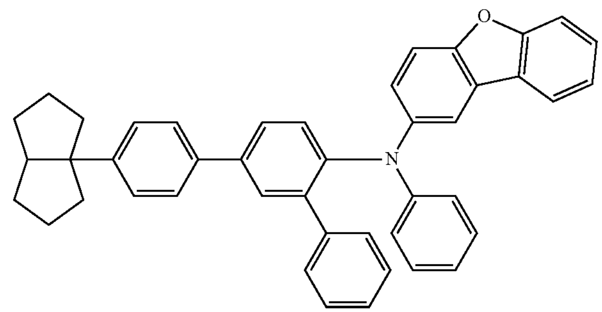 [SMILES: c1ccc(-c2cc(-c3ccc(C45CCCC4CCC5)cc3)ccc2N(c2ccccc2)c2ccc3oc4ccccc4c3c2)cc1] | 25 | 596.3 |
| Compound 126 | 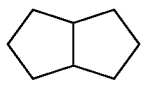 | 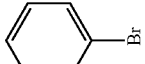 | 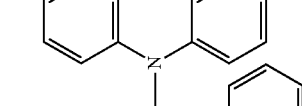 |  | 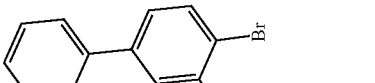 | 32 | 624.3 |

TABLE 2-continued
Structure, raw material, yield and mass spectrum characterization of various compounds
| Compound Number | Reactant A | Reactant B | Reactant C | Reactant D | Compound structure | Yield (%) | m/z [M + H]+ |
|---|---|---|---|---|---|---|---|
| Compound 133 |  | 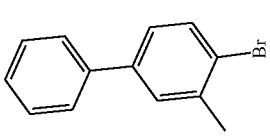 | 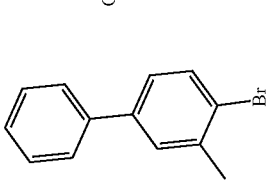 | 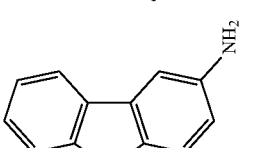 | 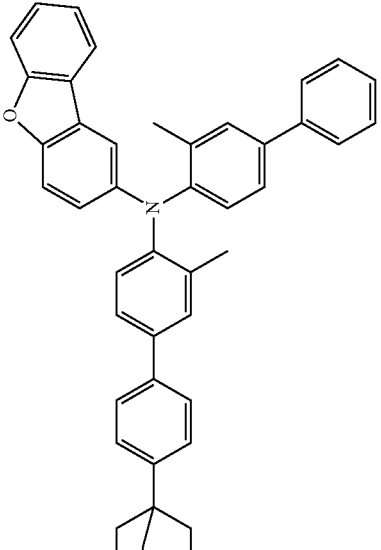 | 39 | 610.3 |
| Compound 199 |  | 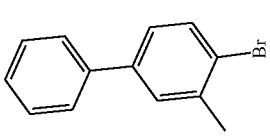 | 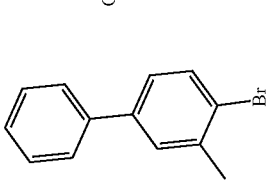 | 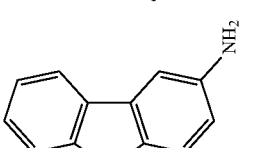 | 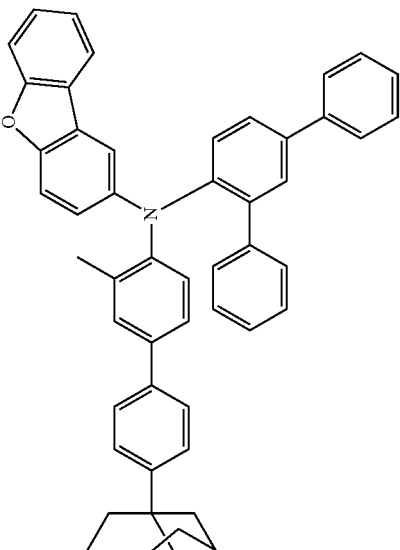 | 48 | 712.4 |

TABLE 2-continued

Structure, raw material, yield and mass spectrum characterization of various compounds

| Compound Number | Reactant A | Reactant B | Reactant C | Reactant D | Compound structure | Yield (%) | m/z [M + H]+ |
|---|---|---|---|---|---|---|---|
| Compound 208 | | | | | 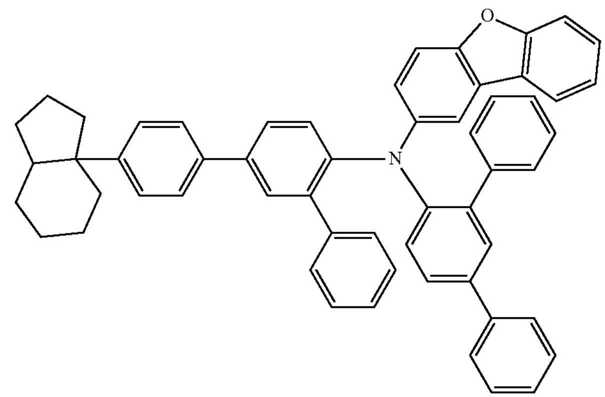 | 54 | 762.4 |
| Compound 229 | | | | | 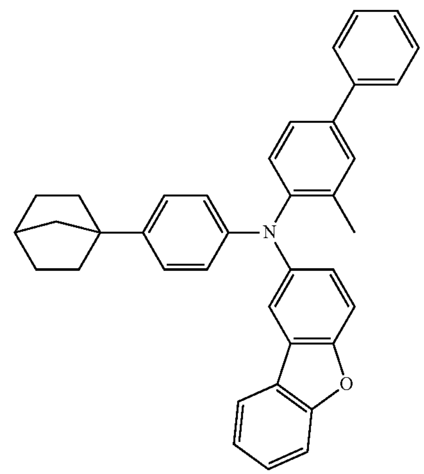 [SMILES: Cc1cc(-c2ccccc2)ccc1N(c1ccc(C23CCC(CC2)C3)cc1)c1ccc2oc3ccccc3c2c1] | 30 | 520.3 |

TABLE 2-continued
Structure, raw material, yield and mass spectrum characterization of various compounds
| Compound Number | Reactant A | Reactant B | Reactant C | Reactant D | Compound structure | Yield (%) | m/z [M + H]+ |
|---|---|---|---|---|---|---|---|
| Compound 243 | 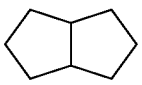 |  |  | 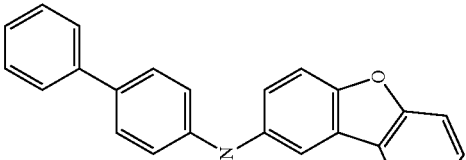 | 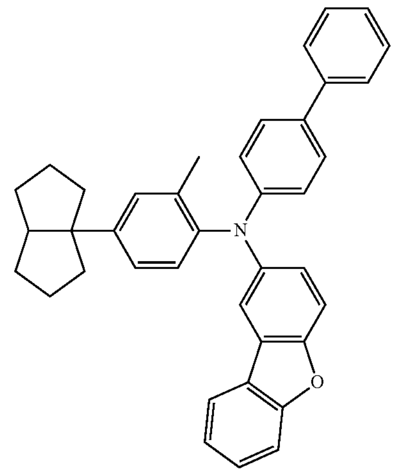 [SMILES: Cc1cc(C23CCCC2CCC3)ccc1N(c1ccc(-c2ccccc2)cc1)c1ccc2oc3ccccc3c2c1] | 59 | 534.3 |
| Compound 327 | 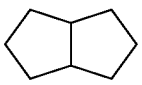 | 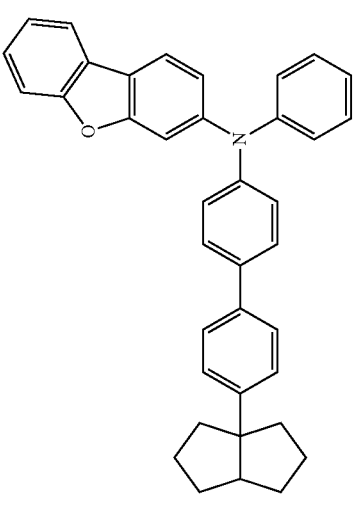 | | | 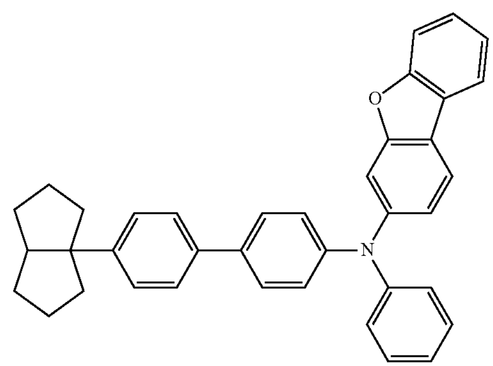 [SMILES: c1ccc(N(c2ccc(-c3ccc(C45CCCC4CCC5)cc3)cc2)c2ccc3c(c2)oc2ccccc23)cc1] | 50 | 520.3 |

TABLE 2-continued
Structure, raw material, yield and mass spectrum characterization of various compounds
| Compound Number | Reactant A | Reactant B | Reactant C | Reactant D | Compound structure | Yield (%) | m/z [M + H]⁺ |
|---|---|---|---|---|---|---|---|
| Compound 392 | 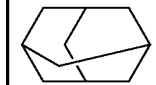 | 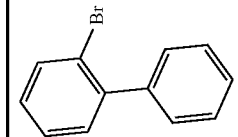 | 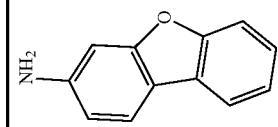 | 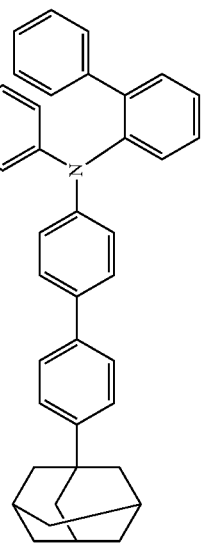 | 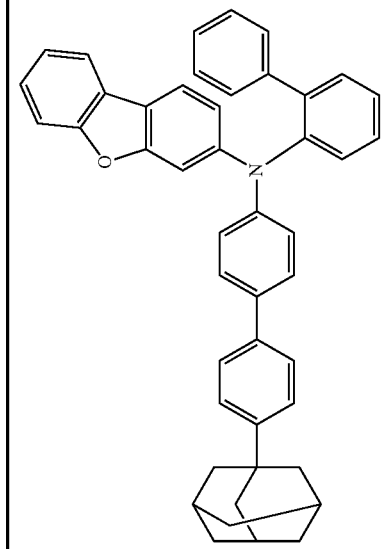 | 36 | 622.3 |
| Compound 466 | 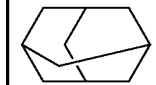 | 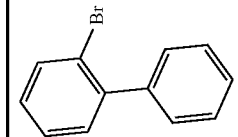 | 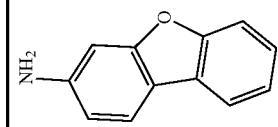 | 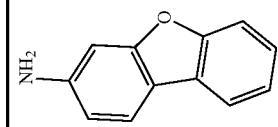 | 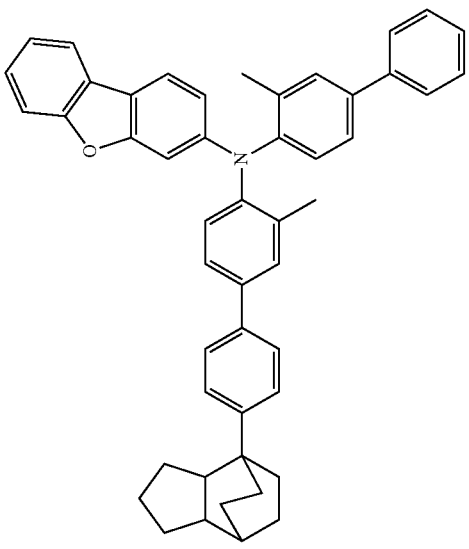 | 40 | 664.4 |

TABLE 2-continued
Structure, raw material, yield and mass spectrum characterization of various compounds
| Compound Number | Reactant A | Reactant B | Reactant C | Reactant D | Compound structure | Yield (%) | m/z [M + H]+ |
|---|---|---|---|---|---|---|---|
| Compound 510 | 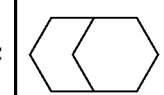 | 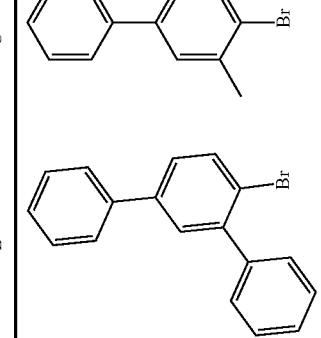 | 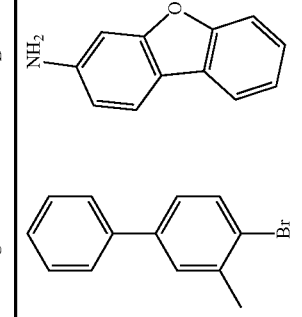 | 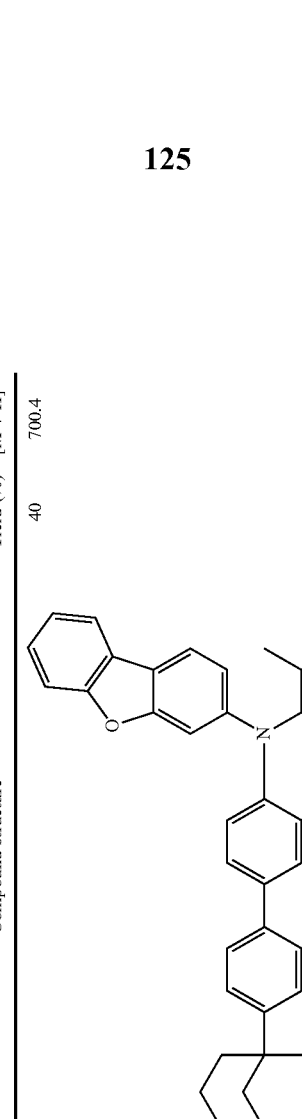 | 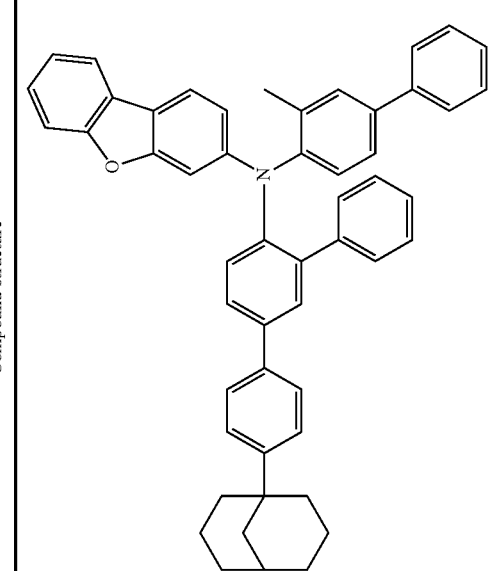 | 40 | 700.4 |
| Compound 613 |  | 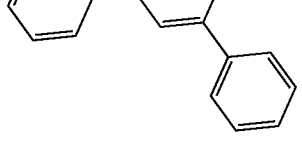 | 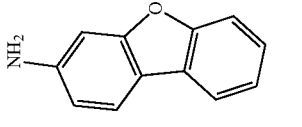 | 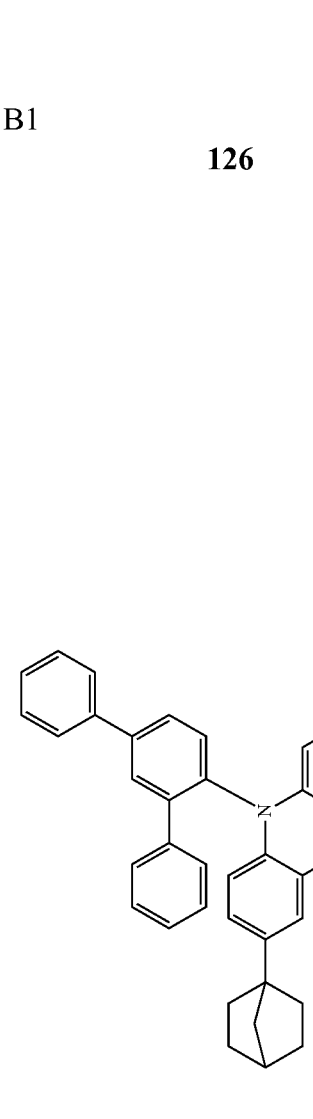 | 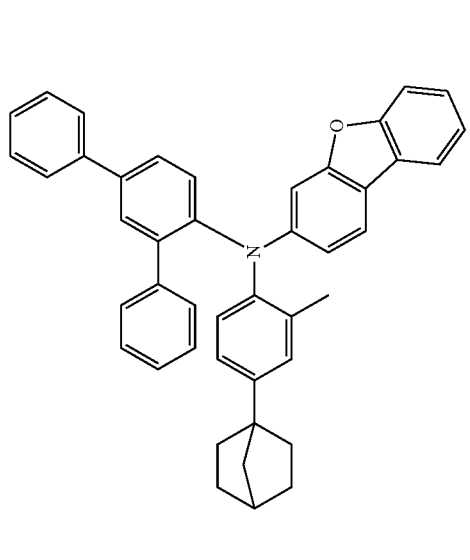 | 30 | 596.3 |

TABLE 2-continued
Structure, raw material, yield and mass spectrum characterization of various compounds
| Compound Number | Reactant A | Reactant B | Reactant C | Reactant D | Compound structure | Yield (%) | m/z [M + H]⁺ |
|---|---|---|---|---|---|---|---|
| Compound 643 | 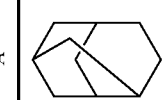 | 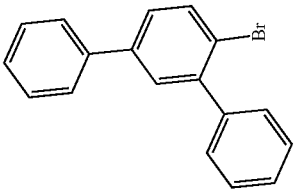 | 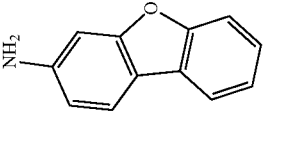 | 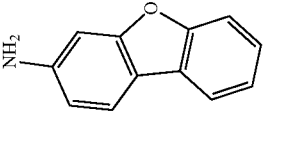 | 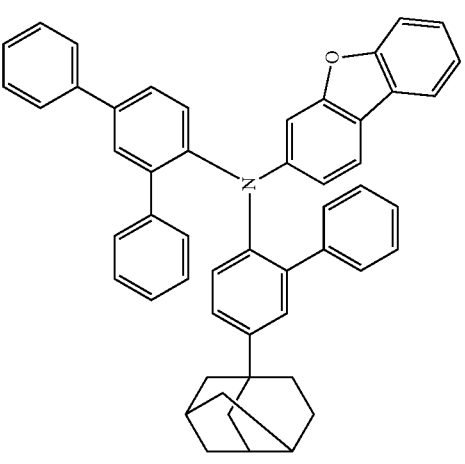 | 44 | 698.3 |
| Compound 774 | 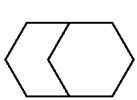 | 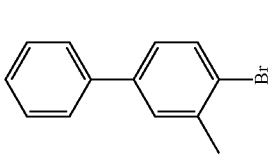 | 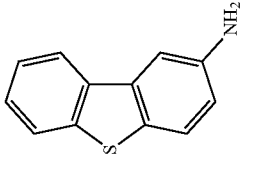 | 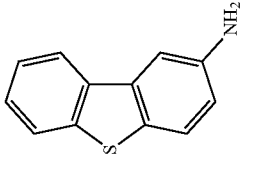 | 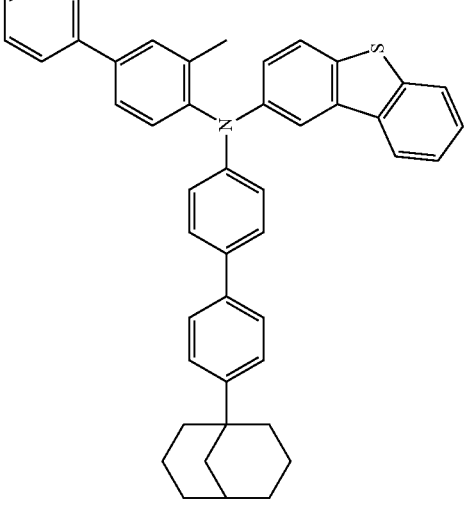 | 41 | 640.3 |

TABLE 2-continued
Structure, raw material, yield and mass spectrum characterization of various compounds
| Compound Number | Reactant A | Reactant B | Reactant C | Reactant D | Compound structure | Yield (%) | m/z [M + H]+ |
|---|---|---|---|---|---|---|---|
| Compound 865 | 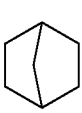 | 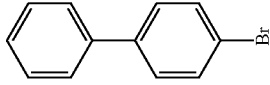 | 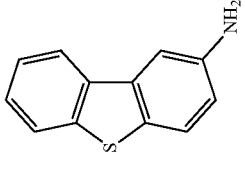 |  | 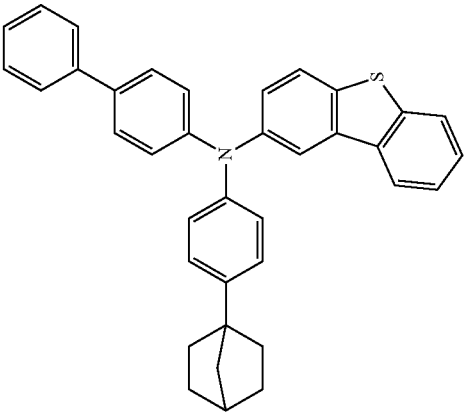 | 38 | 522.2 |
| Compound 926 | 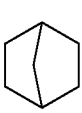 | 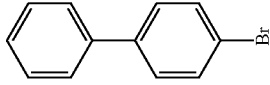 | 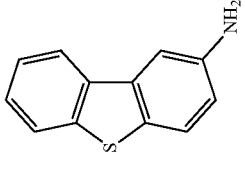 |  | 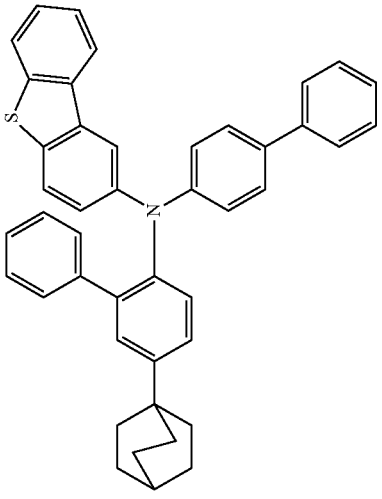 | 27 | 612.3 |

TABLE 2-continued

Structure, raw material, yield and mass spectrum characterization of various compounds

| Compound Number | Reactant A | Reactant B | Reactant C | Reactant D | Compound structure | Yield (%) | m/z [M + H]+ |
|---|---|---|---|---|---|---|---|
| Compound 945 | | | | | 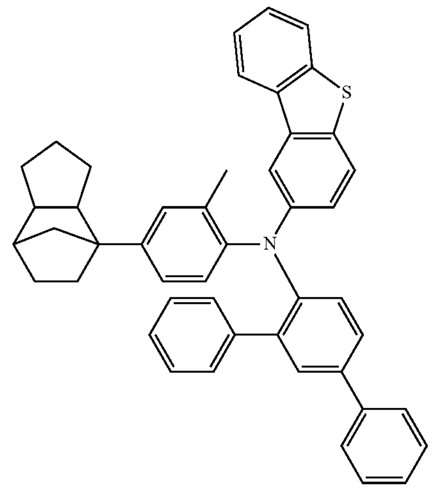 [SMILES: Cc1cc(C23CCC(C2)C2CCCC23)ccc1N(c1ccc2sc3ccccc3c2c1)c1ccc(-c2ccccc2)cc1-c1ccccc1] | 43 | 652.3 |
| Compound 1087 | | | | | 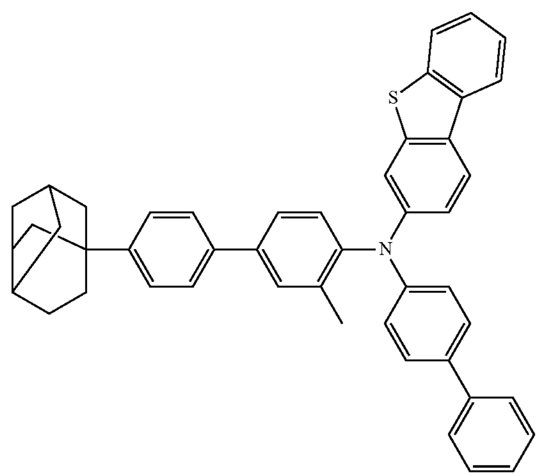 [SMILES: Cc1cc(-c2ccc(C34CCC5CC(CC5C3)C4)cc2)ccc1N(c1ccc(-c2ccccc2)cc1)c1ccc2c(c1)sc1ccccc12] | 54 | 652.3 |

TABLE 2-continued
Structure, raw material, yield and mass spectrum characterization of various compounds
| Compound Number | Reactant A | Reactant B | Reactant C | Reactant D | Compound structure | Yield (%) | m/z [M + H]+ |
|---|---|---|---|---|---|---|---|
| Compound 1253 | 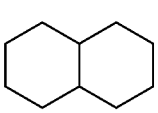 | 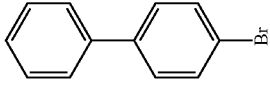 | 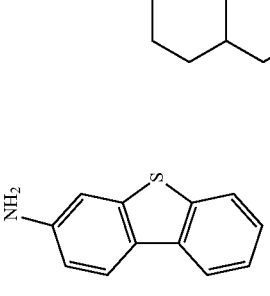 | 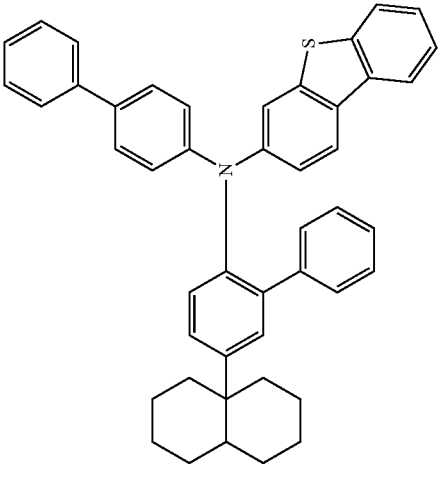 | 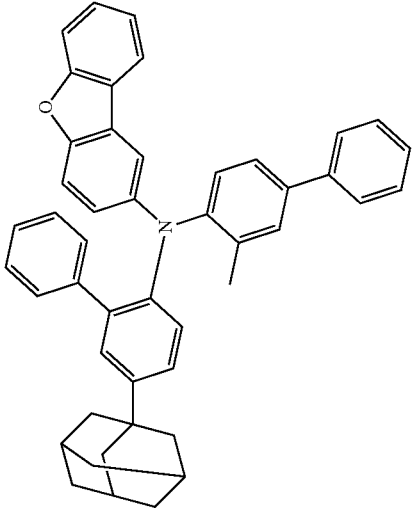 | 38 | 640.3 |
| Compound 269 | 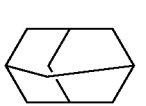 | 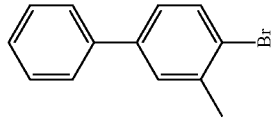 | 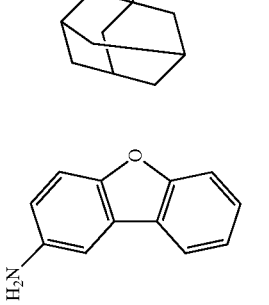 | 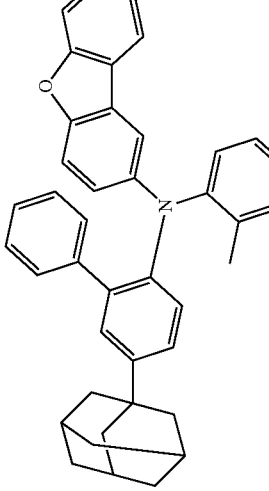 | 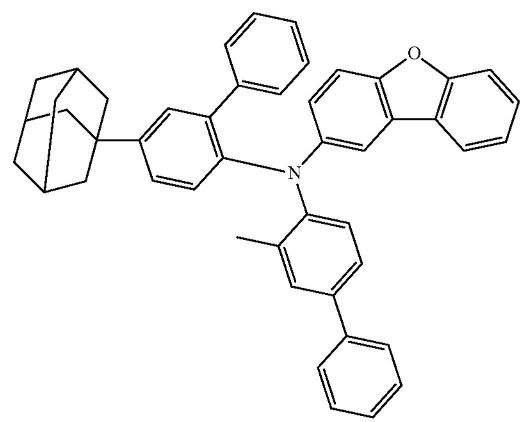 [SMILES: Cc1cc(-c2ccccc2)ccc1N(c1ccc2oc3ccccc3c2c1)c1ccc(C23CC4CC(CC(C4)C2)C3)cc1-c1ccccc1] | 43 | 636.3 |

TABLE 2-continued
Structure, raw material, yield and mass spectrum characterization of various compounds
| Compound Number | Reactant A | Reactant B | Reactant C | Reactant D | Compound structure | Yield (%) | m/z [M + H]+ |
|---|---|---|---|---|---|---|---|
| Compound 521 | | | | | 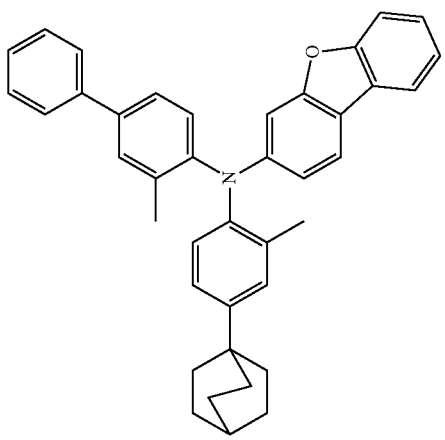 | 37 | 548.3 |

Figure 5:
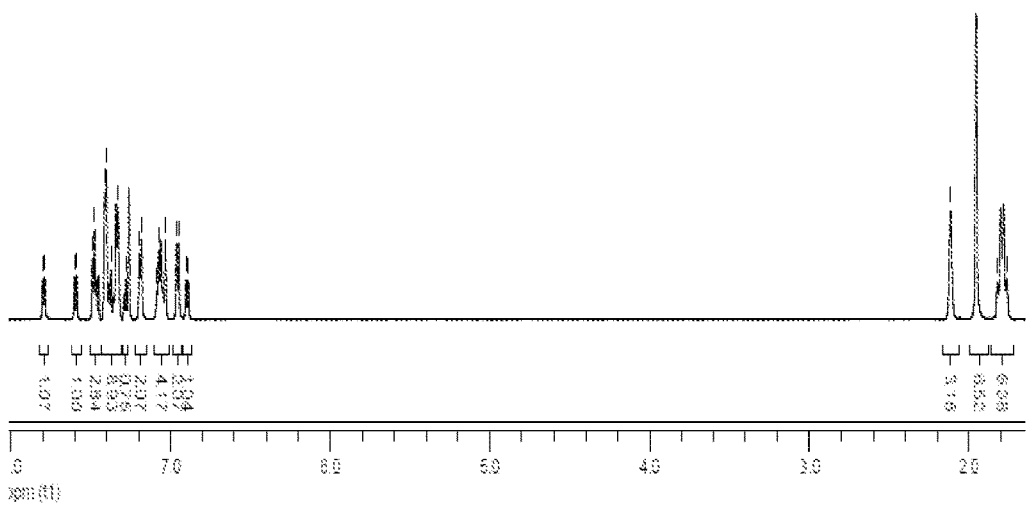
FIG. 5 shows H-NMR of Compound 392.

The NMR spectrum of the compound 392 is as shown in FIG. 5, $^1$H NMR (CDCl$_3$, 400 MHz): 7.80 (d, 1H), 7.59 (d, 1H), 7.49-7.45 (m, 3H), 7.41-7.33 (m, 9H), 7.28 (t, 1H), 7.19 (d, 2H), 7.09-7.03 (m, 4H), 6.96 (d, 2H), 6.90 (d, 1H), 2.12 (s, 3H), 1.95 (s, 6H), 1.82-1.76 (m, 6H).

The following examples are used to describe the application of the compounds of the present disclosure to organic electroluminescent devices.

Example 1

A green organic electroluminescent device was prepared by the following method.

An ITO substrate (made by Corning) with an ITO thickness of 1500 Å was cut into a size of 40 mm(length)×40 mm(width)×0.7 mm(thickness), and was prepared into an experimental substrate with cathode, anode and insulating layer patterns by the photoetching process, and surface treatment was performed by ultraviolet ozone and O$_2$:N$_2$ plasma to increase the work function of the anode (the experimental substrate) and remove scum.

m-MTDATA was subjected to vacuum evaporation on the experimental substrate (the anode) to form a hole injecting layer (HIL) with a thickness of 100 Å, and NPB was subjected to vacuum evaporation on the hole injecting layer to form a first hole transporting layer with a thickness of 1000 Å.

Compound 1 was subjected to vacuum evaporation on the first hole transporting layer to form a second hole transporting layer with a thickness of 400 Å.

CBP as a host material and Ir(ppy)$_3$ as a guest material were subjected to evaporation at the same time according to a film thickness ratio of 100:8 to form a light-emitting layer (EML) with a thickness of 350 Å.

DBimiBphen and LiQ were mixed and evaporated according to a weight ratio of 1:1 to form an electron transporting layer (ETL) with a thickness of 300 Å.

LiQ was evaporated on the electron transporting layer to form an electron injecting layer (EIL) with a thickness of 10 Å.

Magnesium (Mg) and silver (Ag) were mixed at an evaporation rate of 1:9 and were subjected to vacuum evaporation on the electron injecting layer to form a cathode with a thickness of 120 Å.

CP-1 was evaporated with a thickness of 650 Å on the cathode, thereby the preparation of the green organic electroluminescent device was completed.

The structural formulas of m-MTDATA, NPB, CBP, Ir(ppy)$_3$, DBimiBphen, LiQ and CP-1 are as follows:

m-MTDATA
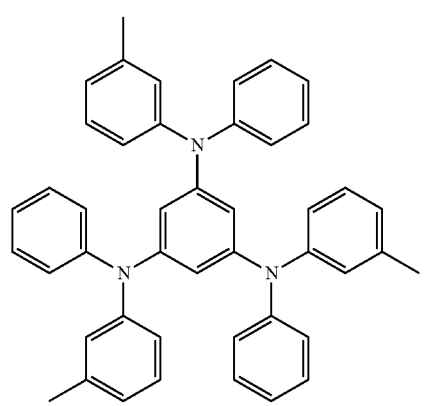

-continued

NPB
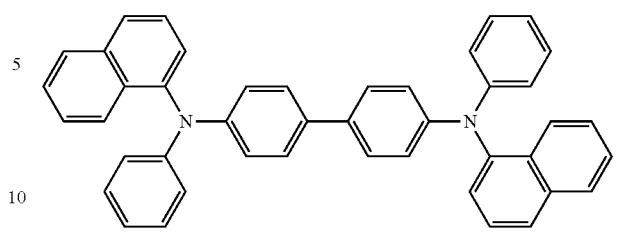

CPB
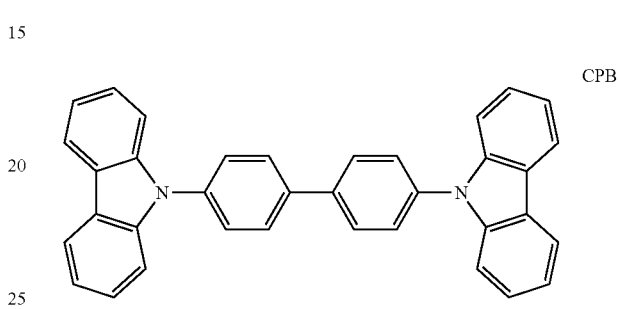

Ir(ppy)$_3$
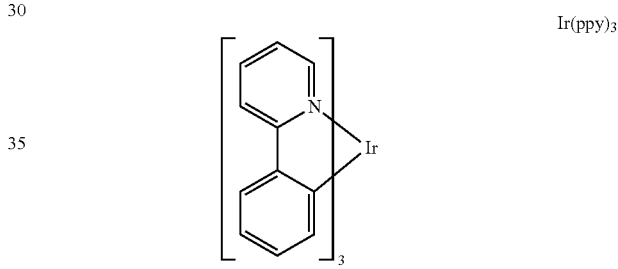

DBimiBphen
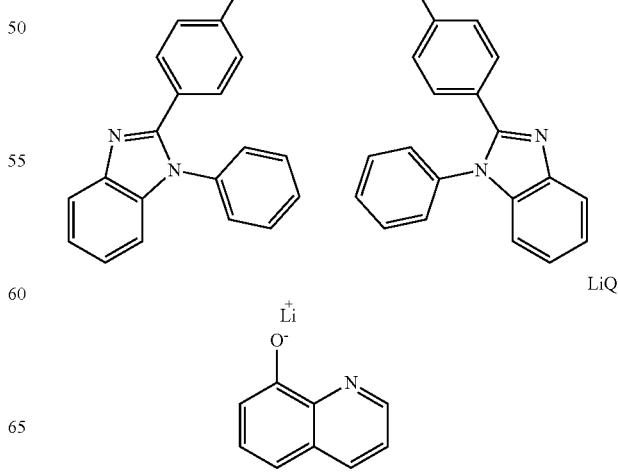

LiQ
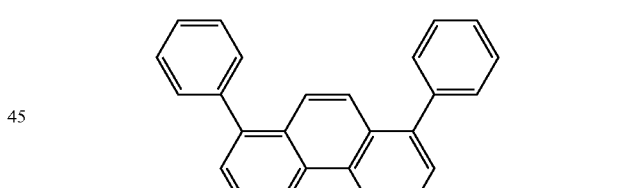

-continued

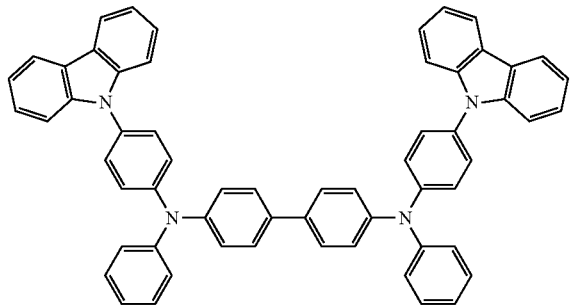

CP-1

Examples 2 to 22

The green organic electroluminescent device was prepared according to the method in Example 1, except that in Examples 2 to 22, the second hole transporting layer material (that is, Compound 1) in Example 1 was replaced with compounds listed in Table 3, respectively, so that the corresponding green organic electroluminescent devices were prepared. For example, in Example 2, Compound 1 in Example 1 was replaced with Compound 51, and the green organic electroluminescent device was prepared according to the same method as that in Example 1.

Comparative Example 1

Compound 1 in Example 1 was replaced with the compound TCTA, and a green organic electroluminescent device was prepared according to the same method as that in Example 1. The structural formula of TCTA is:

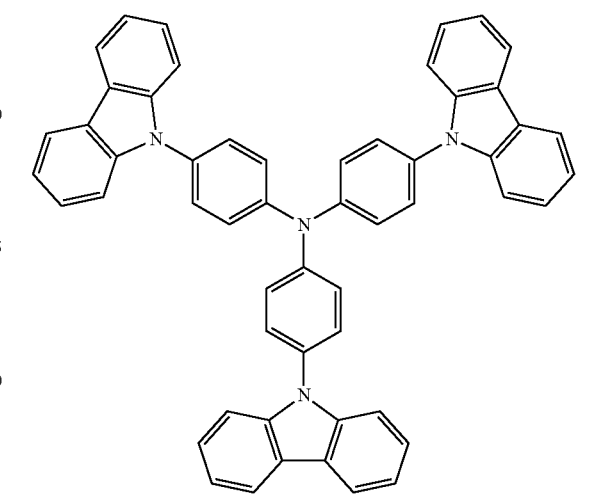

TCTA

For the green organic electroluminescent devices prepared in Examples 1 to 22 and Comparative example 1, the performance of the devices was tested under the condition of 10 mA/cm$^2$, the T95 lifetime of the devices was tested under a constant current density of 20 mA/cm$^2$. The test results are shown in Table 3.

TABLE 3

Performance test results of the organic electroluminescent devices

| Serial number | Second hole transporting layer material | Driving voltage (V) | Current efficiency (Cd/A) | Power efficiency (lm/W) | CIE$_x$ | CIE$_y$ | External quantum efficiency (EQE) (%) | T95 lifetime (h) |
|---|---|---|---|---|---|---|---|---|
| Example 1 | Compound 1 | 3.71 | 76.7 | 65.0 | 0.220 | 0.730 | 15.6 | 306 |
| Example 2 | Compound 51 | 3.63 | 81.8 | 70.8 | 0.220 | 0.730 | 17.0 | 335 |
| Example 3 | Compound 126 | 3.75 | 70.9 | 59.4 | 0.220 | 0.730 | 14.3 | 320 |
| Example 4 | Compound 133 | 4.02 | 86.9 | 67.9 | 0.220 | 0.730 | 20.9 | 360 |
| Example 5 | Compound 199 | 4.01 | 86.5 | 67.8 | 0.220 | 0.730 | 20.8 | 375 |
| Example 6 | Compound 208 | 3.99 | 84.2 | 66.3 | 0.220 | 0.730 | 20.2 | 352 |
| Example 7 | Compound 229 | 3.83 | 72.2 | 59.2 | 0.220 | 0.730 | 14.2 | 316 |
| Example 8 | Compound 243 | 3.77 | 65.6 | 54.7 | 0.220 | 0.730 | 13.1 | 322 |
| Example 9 | Compound 327 | 3.99 | 73.4 | 57.8 | 0.220 | 0.730 | 13.9 | 315 |
| Example 10 | Compound 392 | 3.67 | 69.1 | 59.1 | 0.220 | 0.730 | 14.2 | 292 |
| Example 11 | Compound 466 | 4.01 | 88.1 | 69.0 | 0.220 | 0.730 | 21.1 | 358 |
| Example 12 | Compound 510 | 3.97 | 84.6 | 67.0 | 0.220 | 0.730 | 20.3 | 351 |
| Example 13 | Compound 613 | 3.90 | 86.8 | 69.9 | 0.220 | 0.730 | 20.8 | 364 |
| Example 14 | Compound 643 | 4.05 | 87.9 | 68.1 | 0.220 | 0.730 | 21.1 | 362 |
| Example 15 | Compound 774 | 3.83 | 76.8 | 63.0 | 0.220 | 0.730 | 15.1 | 300 |

TABLE 3-continued

Performance test results of the organic electroluminescent devices

| Serial number | Second hole transporting layer material | Driving voltage (V) | Current efficiency (Cd/A) | Power efficiency (lm/W) | $CIE_x$ | $CIE_y$ | External quantum efficiency (EQE) (%) | T95 lifetime (h) |
|---|---|---|---|---|---|---|---|---|
| Example 16 | Compound 865 | 3.82 | 71.6 | 58.9 | 0.220 | 0.730 | 14.2 | 292 |
| Example 17 | Compound 926 | 3.96 | 67.4 | 53.5 | 0.220 | 0.730 | 12.9 | 323 |
| Example 18 | Compound 945 | 3.98 | 86.3 | 68.1 | 0.220 | 0.730 | 20.7 | 346 |
| Example 19 | Compound 1087 | 3.61 | 69.2 | 60.2 | 0.22 | 0.730 | 16.6 | 311 |
| Example 20 | Compound 1253 | 3.66 | 69.1 | 59.3 | 0.22 | 0.730 | 16.6 | 305 |
| Example 21 | Compound 269 | 3.99 | 88.0 | 69.3 | 0.22 | 0.730 | 21.1 | 361 |
| Example 22 | Compound 521 | 3.95 | 86.5 | 68.8 | 0.22 | 0.730 | 20.8 | 367 |
| Comparative example 1 | TCTA | 4.22 | 52.7 | 39.2 | 0.22 | 0.730 | 12.7 | 210 |

It can be seen from Table 3 that compared with the organic electroluminescent device prepared in Comparative example 1, for the organic electroluminescent devices in Examples 1 to 22, the driving voltage is reduced by about 4%-14%, the current efficiency is increased by about 24%-67%, the power efficiency is increased by about 36%-81%, the external quantum efficiency is increased by about 3.1%-66%, and the life is increased by about 39%-79%. In addition, compared with other examples, the organic electroluminescent devices in Examples 4 to 5, 11 to 14, 18 and 21 to 22 also have longer life and higher efficiency, for example, the lifetime is maximally increased by 28%, and the current efficiency is maximally increased by 34%.

Part of the nitrogen-containing compound structure of the present disclosure introduces cycloalkane with the three-dimensional structure and dibenzofuran/dibenzothiophene into the triarylamine basic structure at the same time. The dibenzofuran/dibenzothiophene group has stronger electron dissociation energy, which can effectively reduce the HOMO energy level of the material, so that the holes can be injected into the green light-emitting layer more smoothly, the driving voltage of the organic electroluminescent device is effectively reduced, and the luminous efficiency is improved, but this type structure has a larger conjugate plane, which may cause intermolecular stacking and crystallization to reduce the life of the device. Through the introduction of the three-dimensional cycloalkane with large steric hindrance, the stacking effect is effectively reduced, the film-forming performance of the material is greatly improved, and the life of the device is not reduced, but is prolonged. In addition, in the preferred embodiment of the present application, a specific substituent is introduced at the ortho-position of the nitrogen atom on the aryl group, so that the planarity of the triarylamine core group can be reduced, the HOMO energy level can be further improved, and the intermolecular stacking effect can be reduced. Therefore, the nitrogen-containing compound of the present application is suitable for the hole transporting layer of the organic electroluminescent device, particularly suitable for the second hole transporting layer of the organic electroluminescent device, so that the driving voltage drop of the organic electroluminescent device can be reduced, the current efficiency, the power efficiency and the external quantum efficiency of the organic electroluminescent device can be improved, and the life of the organic electroluminescent device can be prolonged.

It should be understood that the present disclosure does not limit the application to the detailed structure and the arrangement manner of the parts provided in the description. The present disclosure can have other embodiments, and can be implemented and performed in various manners. The aforementioned variation and modification forms should fall within the scope of the present application. It should be understood that the present application disclosed and defined in the description extends to all replaceable combinations of two or more independent features mentioned or obvious herein and/or in the accompanying drawings. All the different combinations form a plurality of replaceable aspects of the present disclosure. The embodiments described in the description illustrate the known preferred manners for implementing the present disclosure, and those skilled in the art can utilize the present disclosure.

What is claimed is:

1. A nitrogen-containing compound, wherein the structure of the nitrogen-containing compound is shown as Chemical formula 1:

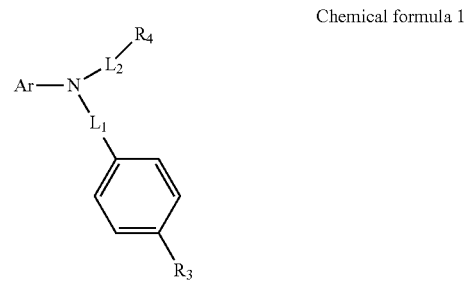

Chemical formula 1 wherein Ar is selected from 2-DBF, 3-DBF, 2-DBT or 3-DBT; and the structural formulas of 2-DBF, 3-DBF, 2-DBT and 3-DBT are as follows:

2-DBF

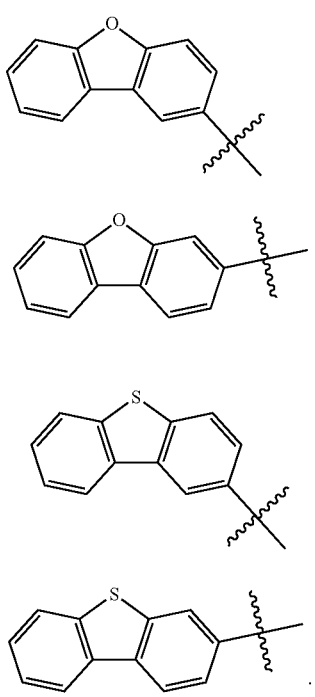

3-DBF

2-DBT

3-DBT $L_1$ is

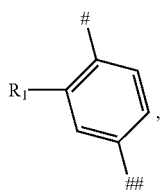

and in $L_1$, "#" represents a connection point between the phenylene of $L_1$ and N, and "##" represents a connection point between the phenylene of $L_1$ and

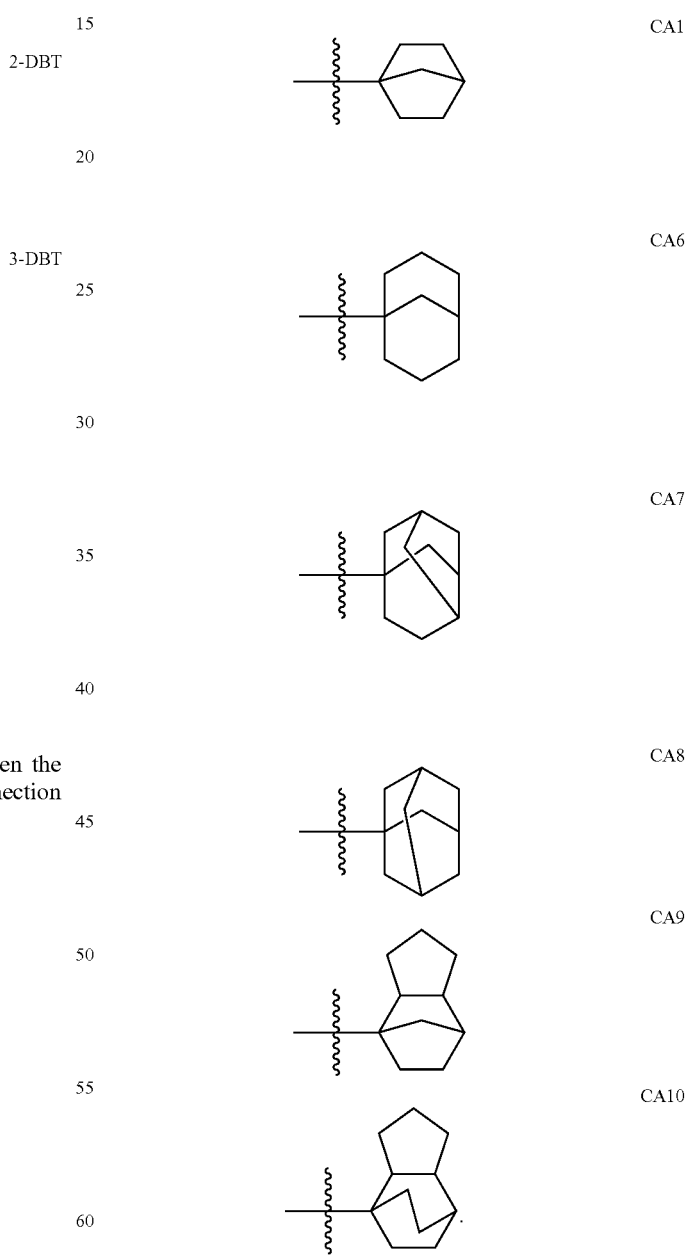

$L_2$ is

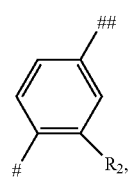

and in $L_2$, "#" represents a connection point between the phenylene of $L_2$ and N, and "##" represents a connection point between the phenylene of $L_2$ and $R_4$;

$R_1$ is selected from methyl or phenyl; $R_2$ is selected from methyl or phenyl;

$R_3$ is selected from H and the groups shown in CA1, CA6 to CA10; $R_4$ is selected from phenyl and the substituents shown in CA1, CA6 to CA10; only one of $R_3$ and $R_4$ is selected from the substituents shown in CA1, CA6 to CA10; where the structures of CA1, CA6 to CA10 are as follows:

2. The nitrogen-containing compound according to claim 1, wherein the nitrogen-containing compound is selected from the group consisting of various compounds listed in the following table:

| Substituent of compound | Ar | L₁ | R₃ | R₄ | L₂ |
|---|---|---|---|---|---|
| Compound 115 | 2-DBF | (dimethylphenylene, # top, ## bottom) | CA6 | Ph | (dimethylphenylene, ## top, # bottom) |
| Compound 116 | 2-DBF | (dimethylphenylene, # top, ## bottom) | CA9 | Ph | (dimethylphenylene, ## top, # bottom) |
| Compound 117 | 2-DBF | (dimethylphenylene, # top, ## bottom) | CA10 | Ph | (dimethylphenylene, ## top, # bottom) |
| Compound 133 | 2-DBF | (dimethylphenylene, # top, ## bottom) | CA1 | Ph | (dimethylphenylene, ## top, # bottom) |
| Compound 155 | 2-DBF | (biphenyl, # top, ## bottom) | CA1 | Ph | (dimethylphenylene, ## top, # bottom) |
| Compound 160 | 2-DBF | (biphenyl, # top, ## bottom) | CA6 | Ph | (dimethylphenylene, ## top, # bottom) |
| Compound 163 | 2-DBF | (biphenyl, # top, ## bottom) | CA9 | Ph | (dimethylphenylene, ## top, # bottom) |
| Compound 164 | 2-DBF | (biphenyl, # top, ## bottom) | CA10 | Ph | (dimethylphenylene, ## top, # bottom) |

-continued
| Substituent of compound | Ar | L₁ | R₃ | R₄ | L₂ |
|---|---|---|---|---|---|
| Compound 167 | 2-DBF | 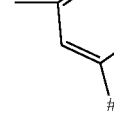 | CA1 | Ph | 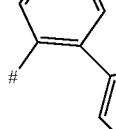 |
| Compound 172 | 2-DBF | 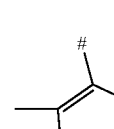 | CA6 | Ph | 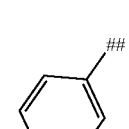 |
| Compound 173 | 2-DBF | 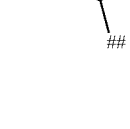 | CA8 | Ph | 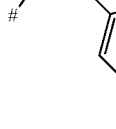 |
| Compound 174 | 2-DBF | 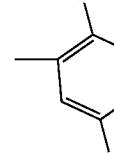 | CA9 | Ph | 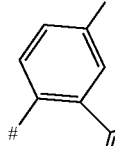 |
| Compound 176 | 2-DBF |  | CA1 | Ph | 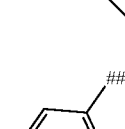 |
| Compound 180 | 2-DBF | 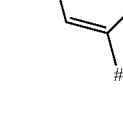 | CA6 | Ph | 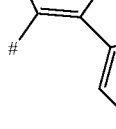 |

-continued

| Substituent of compound | Ar | L₁ | R₃ | R₄ | L₂ |
|---|---|---|---|---|---|
| Compound 181 | 2-DBF | | CA7 | Ph | |
| Compound 182 | 2-DBF | | CA8 | Ph | |
| Compound 183 | 2-DBF | | CA9 | Ph | |
| Compound 184 | 2-DBF | | CA10 | Ph | |
| Compound 199 | 2-DBF | | CA7 | Ph | |
| Compound 208 | 2-DBF | | CA4 | Ph | |

-continued

| Substituent of compound | Ar | L₁ | R₃ | R₄ | L₂ |
|---|---|---|---|---|---|
| Compound 218 | 2-DBF | (dimethylphenyl with # and ##) | H | CA1 | (dimethylphenyl with ## and #) |
| Compound 223 | 2-DBF | (dimethylphenyl with # and ##) | H | CA6 | (dimethylphenyl with ## and #) |
| Compound 224 | 2-DBF | (dimethylphenyl with # and ##) | H | CA7 | (dimethylphenyl with ## and #) |
| Compound 225 | 2-DBF | (dimethylphenyl with # and ##) | H | CA8 | (dimethylphenyl with ## and #) |
| Compound 226 | 2-DBF | (dimethylphenyl with # and ##) | H | CA9 | (dimethylphenyl with ## and #) |
| Compound 255 | 2-DBF | (biphenyl with # and ##) | H | CA6 | (dimethylphenyl with ## and #) |
| Compound 256 | 2-DBF | (biphenyl with # and ##) | H | CA7 | (dimethylphenyl with ## and #) |
| Compound 257 | 2-DBF | (biphenyl with # and ##) | H | CA8 | (dimethylphenyl with ## and #) |

-continued

| Substituent of compound | Ar | L₁ | R₃ | R₄ | L₂ |
|---|---|---|---|---|---|
| Compound 258 | 2-DBF | | H | CA9 | |
| Compound 259 | 2-DBF | | H | CA10 | |
| Compound 262 | 2-DBF | | H | CA1 | |
| Compound 267 | 2-DBF | | H | CA6 | |
| Compound 268 | 2-DBF | | H | CA7 | |
| Compound 269 | 2-DBF | | H | CA8 | |

-continued

| Substituent of compound | Ar | L₁ | R₃ | R₄ | L₂ |
|---|---|---|---|---|---|
| Compound 270 | 2-DBF | (methylphenylene, # top, ## bottom) | H | CA9 | (biphenylene, ## top, # bottom) |
| Compound 271 | 2-DBF | (methylphenylene, # top, ## bottom) | H | CA10 | (biphenylene, ## top, # bottom) |
| Compound 274 | 2-DBF | (biphenylene, # top, ## bottom) | H | CA1 | (biphenylene, ## top, # bottom) |
| Compound 279 | 2-DBF | (biphenylene, # top, ## bottom) | H | CA6 | (biphenylene, ## top, # bottom) |
| Compound 280 | 2-DBF | (biphenylene, # top, ## bottom) | H | CA7 | (biphenylene, ## top, # bottom) |
| Compound 281 | 2-DBF | (biphenylene, # top, ## bottom) | H | CA8 | (biphenylene, ## top, # bottom) |

-continued

| Substituent of compound | Ar | L₁ | R₃ | R₄ | L₂ |
|---|---|---|---|---|---|
| Compound 282 | 2-DBF | biphenyl (#, ##) | H | CA9 | biphenyl (##, #) |
| Compound 283 | 2-DBF | biphenyl (#, ##) | H | CA10 | biphenyl (##, #) |
| Compound 408 | 3-DBF | methylphenyl (#, ##) | CA1 | Ph | methylphenyl (##, #) |
| Compound 412 | 3-DBF | methylphenyl (#, ##) | CA7 | Ph | methylphenyl (##, #) |
| Compound 413 | 3-DBF | methylphenyl (#, ##) | CA8 | Ph | methylphenyl (##, #) |
| Compound 414 | 3-DBF | methylphenyl (#, ##) | CA9 | Ph | methylphenyl (##, #) |
| Compound 451 | 3-DBF | biphenyl (#, ##) | CA1 | Ph | methylphenyl (##, #) |

-continued

| Substituent of compound | Ar | L₁ | R₃ | R₄ | L₂ |
|---|---|---|---|---|---|
| Compound 457 | 3-DBF | biphenyl (# ortho, ## meta) | CA7 | Ph | dimethylphenyl (## para, # ortho) |
| Compound 458 | 3-DBF | biphenyl (# ortho, ## meta) | CA9 | Ph | dimethylphenyl (## para, # meta) |
| Compound 459 | 3-DBF | biphenyl (# ortho, ## meta) | CA10 | Ph | dimethylphenyl (## para, # meta) |
| Compound 462 | 3-DBF | methylphenyl (# para, ## meta) | CA1 | Ph | biphenyl (## meta, # ortho) |
| Compound 466 | 3-DBF | methylphenyl (# para, ## meta) | CA10 | Ph | methylphenyl (## para, # meta) |
| Compound 468 | 3-DBF | methylphenyl (# para, ## meta) | CA8 | Ph | biphenyl (## meta, # ortho) |
| Compound 469 | 3-DBF | methylphenyl (# para, ## meta) | CA9 | Ph | biphenyl (## meta, # ortho) |

-continued

| Substituent of compound | Ar | L₁ | R₃ | R₄ | L₂ |
|---|---|---|---|---|---|
| Compound 470 | 3-DBF | (2-methyl-1,4-phenylene) | CA10 | Ph | (biphenyl-3,5-diyl) |
| Compound 471 | 3-DBF | (biphenyl-2,5-diyl) | CA1 | Ph | (biphenyl-3,5-diyl) |
| Compound 476 | 3-DBF | (biphenyl-2,5-diyl) | CA6 | Ph | (biphenyl-3,5-diyl) |
| Compound 477 | 3-DBF | (biphenyl-2,5-diyl) | CA7 | Ph | (biphenyl-3,5-diyl) |
| Compound 478 | 3-DBF | (biphenyl-2,5-diyl) | CA8 | Ph | (biphenyl-3,5-diyl) |
| Compound 479 | 3-DBF | (biphenyl-2,5-diyl) | CA9 | Ph | (biphenyl-3,5-diyl) |

-continued

| Substituent of compound | Ar | L₁ | R₃ | R₄ | L₂ |
|---|---|---|---|---|---|
| Compound 480 | 3-DBF | biphenyl (#, ##) | CA10 | Ph | biphenyl (##, #) |
| Compound 510 | 3-DBF | biphenyl (#, ##) | CA6 | Ph | methylphenyl (##, #) |
| Compound 512 | 3-DBF | biphenyl (#, ##) | CA8 | Ph | methylphenyl (##, #) |
| Compound 520 | 3-DBF | methylphenyl (#, ##) | H | CA1 | methylphenyl (##, #) |
| Compound 525 | 3-DBF | methylphenyl (#, ##) | H | CA6 | methylphenyl (##, #) |
| Compound 526 | 3-DBF | methylphenyl (#, ##) | H | CA7 | methylphenyl (##, #) |
| Compound 527 | 3-DBF | methylphenyl (#, ##) | H | CA8 | methylphenyl (##, #) |

-continued

| Substituent of compound | Ar | L₁ | R₃ | R₄ | L₂ |
|---|---|---|---|---|---|
| Compound 528 | 3-DBF | (2-methyl-1,4-phenylene, # at 1, ## at 4) | H | CA9 | (3-methyl-1,4-phenylene, ## at 1, # at 4) |
| Compound 529 | 3-DBF | (2-methyl-1,4-phenylene, # at 1, ## at 4) | H | CA10 | (3-methyl-1,4-phenylene, ## at 1, # at 4) |
| Compound 562 | 3-DBF | (biphenyl-2,5-diyl, # at 2, ## at 5) | H | CA6 | (3-methyl-1,4-phenylene, ## at 1, # at 4) |
| Compound 563 | 3-DBF | (biphenyl-2,5-diyl, # at 2, ## at 5) | H | CA7 | (3-methyl-1,4-phenylene, ## at 1, # at 4) |
| Compound 564 | 3-DBF | (biphenyl-2,5-diyl, # at 2, ## at 5) | H | CA8 | (3-methyl-1,4-phenylene, ## at 1, # at 4) |
| Compound 565 | 3-DBF | (biphenyl-2,5-diyl, # at 2, ## at 5) | H | CA9 | (3-methyl-1,4-phenylene, ## at 1, # at 4) |
| Compound 566 | 3-DBF | (biphenyl-2,5-diyl, # at 2, ## at 5) | H | CA10 | (3-methyl-1,4-phenylene, ## at 1, # at 4) |

-continued

| Substituent of compound | Ar | L₁ | R₃ | R₄ | L₂ |
|---|---|---|---|---|---|
| Compound 569 | 3-DBF | (structure) | H | CA1 | (structure) |
| Compound 574 | 3-DBF | (structure) | H | CA6 | (structure) |
| Compound 575 | 3-DBF | (structure) | H | CA7 | (structure) |
| Compound 576 | 3-DBF | (structure) | H | CA8 | (structure) |
| Compound 577 | 3-DBF | (structure) | H | CA9 | (structure) |
| Compound 578 | 3-DBF | (structure) | H | CA10 | (structure) |

-continued

| Substituent of compound | Ar | L₁ | R₃ | R₄ | L₂ |
|---|---|---|---|---|---|
| Compound 581 | 3-DBF | (biphenyl, # top, ## bottom) | H | CA1 | (biphenyl, ## top, # bottom) |
| Compound 586 | 3-DBF | (biphenyl, # top, ## bottom) | H | CA6 | (biphenyl, ## top, # bottom) |
| Compound 587 | 3-DBF | (biphenyl, # top, ## bottom) | H | CA8 | (biphenyl, ## top, # bottom) |
| Compound 588 | 3-DBF | (biphenyl, # top, ## bottom) | H | CA9 | (biphenyl, ## top, # bottom) |
| Compound 589 | 3-DBF | (biphenyl, # top, ## bottom) | H | CA10 | (biphenyl, ## top, # bottom) |
| Compound 613 | 3-DBF | (biphenyl, # top, ## bottom) | H | CA1 | (methylphenyl, ## top, # bottom) |

-continued

| Substituent of compound | Ar | L₁ | R₃ | R₄ | L₂ |
|---|---|---|---|---|---|
| Compound 643 | 3-DBF | (2-phenylphenyl-5-yl, # and ##) | H | CA7 | (biphenyl group, ## and #) |
| Compound 725 | 2-DBT | (3-methylphenyl-1,4-diyl, # and ##) | CA1 | Ph | (3-methylphenyl-1,4-diyl, ## and #) |
| Compound 730 | 2-DBT | (3-methylphenyl-1,4-diyl, # and ##) | CA6 | Ph | (3-methylphenyl-1,4-diyl, ## and #) |
| Compound 731 | 2-DBT | (3-methylphenyl-1,4-diyl, # and ##) | CA7 | Ph | (3-methylphenyl-1,4-diyl, ## and #) |
| Compound 732 | 2-DBT | (3-methylphenyl-1,4-diyl, # and ##) | CA8 | Ph | (3-methylphenyl-1,4-diyl, ## and #) |
| Compound 737 | 2-DBT | (3-methylphenyl-1,4-diyl, # and ##) | CA9 | Ph | (3-methylphenyl-1,4-diyl, ## and #) |
| Compound 738 | | (3-methylphenyl-1,4-diyl, # and ##) | CA10 | Ph | (3-methylphenyl-1,4-diyl, ## and #) |

-continued

| Substituent of compound | Ar | L₁ | R₃ | R₄ | L₂ |
|---|---|---|---|---|---|
| Compound 782 | 2-DBT | biphenyl (#, ##) | CA1 | Ph | methylphenyl (##, #) |
| Compound 787 | 2-DBT | biphenyl (#, ##) | CA6 | Ph | methylphenyl (##, #) |
| Compound 788 | 2-DBT | biphenyl (#, ##) | CA7 | Ph | methylphenyl (##, #) |
| Compound 789 | 2-DBT | biphenyl (#, ##) | CA8 | Ph | methylphenyl (##, #) |
| Compound 790 | 2-DBT | biphenyl (#, ##) | CA9 | Ph | methylphenyl (##, #) |
| Compound 791 | 2-DBT | biphenyl (#, ##) | CA10 | Ph | methylphenyl (##, #) |
| Compound 795 | 2-DBT | methylphenyl (#, ##) | CA1 | Ph | biphenyl (##, #) |

-continued

| Substituent of compound | Ar | L₁ | R₃ | R₄ | L₂ |
|---|---|---|---|---|---|
| Compound 800 | 2-DBT | (2-methylphenylene, # at 1, ## at 4) | CA6 | Ph | (1,1'-biphenyl-3,5-diyl) |
| Compound 801 | 2-DBT | (2-methylphenylene, # at 1, ## at 4) | CA7 | Ph | (1,1'-biphenyl-3,5-diyl) |
| Compound 802 | 2-DBT | (2-methylphenylene, # at 1, ## at 4) | CA8 | Ph | (1,1'-biphenyl-3,5-diyl) |
| Compound 803 | 2-DBT | (2-methylphenylene, # at 1, ## at 4) | CA9 | Ph | (1,1'-biphenyl-3,5-diyl) |
| Compound 804 | 2-DBT | (2-methylphenylene, # at 1, ## at 4) | CA10 | Ph | (1,1'-biphenyl-3,5-diyl) |
| Compound 807 | 2-DBT | (2-phenylphenylene, # at 1, ## at 4) | CA1 | Ph | (1,1'-biphenyl-3,5-diyl) |

-continued

| Substituent of compound | Ar | L₁ | R₃ | R₄ | L₂ |
|---|---|---|---|---|---|
| Compound 812 | 2-DBT | biphenyl (#, ##) | CA6 | Ph | biphenyl (##, #) |
| Compound 813 | 2-DBT | biphenyl (#, ##) | CA7 | Ph | biphenyl (##, #) |
| Compound 814 | 2-DBT | biphenyl (#, ##) | CA8 | Ph | biphenyl (##, #) |
| Compound 815 | 2-DBT | biphenyl (#, ##) | CA9 | Ph | biphenyl (##, #) |
| Compound 816 | 2-DBT | biphenyl (#, ##) | CA10 | Ph | biphenyl (##, #) |
| Compound 857 | 2-DBT | methylphenyl (#, ##) | H | CA1 | methylphenyl (##, #) |

-continued

| Substituent of compound | Ar | L₁ | R₃ | R₄ | L₂ |
|---|---|---|---|---|---|
| Compound 864 | 2-DBT | (phenyl, # top, ## bottom) | H | CA6 | (phenyl, ## top, # bottom) |
| Compound 866 | 2-DBT | (phenyl, # top, ## bottom) | H | CA7 | (phenyl, ## top, # bottom) |
| Compound 867 | 2-DBT | (phenyl, # top, ## bottom) | H | CA8 | (phenyl, ## top, # bottom) |
| Compound 868 | 2-DBT | (phenyl, # top, ## bottom) | H | CA9 | (phenyl, ## top, # bottom) |
| Compound 869 | 2-DBT | (phenyl, # top, ## bottom) | H | CA10 | (phenyl, ## top, # bottom) |
| Compound 901 | 2-DBT | (biphenyl, # top, ## bottom) | H | CA1 | (phenyl, ## top, # bottom) |
| Compound 906 | 2-DBT | (biphenyl, # top, ## bottom) | H | CA6 | (phenyl, ## top, # bottom) |
| Compound 907 | 2-DBT | (biphenyl, # top, ## bottom) | H | CA7 | (phenyl, ## top, # bottom) |

-continued

| Substituent of compound | Ar | L₁ | R₃ | R₄ | L₂ |
|---|---|---|---|---|---|
| Compound 908 | 2-DBT | biphenyl (# / ##) | H | CA8 | dimethylphenyl (## / #) |
| Compound 909 | 2-DBT | biphenyl (# / ##) | H | CA10 | dimethylphenyl (## / #) |
| Compound 912 | 2-DBT | methylphenyl (# / ##) | H | CA1 | biphenyl (## / #) |
| Compound 917 | 2-DBT | methylphenyl (# / ##) | H | CA6 | biphenyl (## / #) |
| Compound 918 | 2-DBT | methylphenyl (# / ##) | H | CA7 | biphenyl (## / #) |
| Compound 919 | 2-DBT | methylphenyl (# / ##) | H | CA8 | biphenyl (## / #) |

-continued

| Substituent of compound | Ar | L₁ | R₃ | R₄ | L₂ |
|---|---|---|---|---|---|
| Compound 920 | 2-DBT | (methylphenylene, # top, ## bottom) | H | CA9 | (biphenyl linker, ## top, # bottom) |
| Compound 921 | 2-DBT | (methylphenylene, # top, ## bottom) | H | CA10 | (biphenyl linker, ## top, # bottom) |
| Compound 924 | 2-DBT | (biphenylene, # top, ## bottom) | H | CA1 | (biphenyl linker, ## top, # bottom) |
| Compound 930 | 2-DBT | (biphenylene, # top, ## bottom) | H | CA6 | (biphenyl linker, ## top, # bottom) |
| Compound 931 | 2-DBT | (biphenylene, # top, ## bottom) | H | CA7 | (biphenyl linker, ## top, # bottom) |
| Compound 932 | 2-DBT | (biphenylene, # top, ## bottom) | H | CA8 | (biphenyl linker, ## top, # bottom) |

| Substituent of compound | Ar | L₁ | R₃ | R₄ | L₂ |
|---|---|---|---|---|---|
| Compound 933 | 2-DBT | [biphenyl structure with # and ##] | H | CA9 | [biphenyl structure with ## and #] |
| Compound 934 | 2-DBT | [biphenyl structure with # and ##] | H | CA10 | [biphenyl structure with ## and #] |
| Compound 937 | 3-DBF | [methylphenyl structure with # and ##] | CA6 | Ph | [biphenyl structure with ## and #] |
| Compound 938 | 3-DBF | [methylphenyl structure with # and ##] | CA7 | Ph | [biphenyl structure with ## and #] |
| Compound 941 | 2-DBF | [biphenyl structure with # and ##] | H | CA1 | [methylphenyl structure with ## and #] |
| Compound 945 | 2-DBT | [biphenyl structure with # and ##] | H | CA9 | [dimethylphenyl structure with ## and #] |
| Compound 995 | 2-DBF | [methylphenyl structure with # and ##] | H | CA10 | [dimethylphenyl structure with ## and #] |

-continued

| Substituent of compound | Ar | L₁ | R₃ | R₄ | L₂ |
|---|---|---|---|---|---|
| Compound 1027 | 3-DBT | (para-phenylene, # top, ## bottom) | CA8 | Ph | (2-methyl-1,4-phenylene, ## top, # bottom) |
| Compound 1047 | 2-DBF | (2-methyl-1,4-phenylene, # top, ## bottom) | CA7 | Ph | (2-methyl-1,4-phenylene, ## top, # bottom) |
| Compound 1048 | 2-DBF | (2-methyl-1,4-phenylene, # top, ## bottom) | CA8 | Ph | (2-methyl-1,4-phenylene, ## top, # bottom) |
| Compound 1083 | 2-DBF | (2-methyl-1,4-phenylene, # top, ## bottom) | CA10 | Ph | (2-phenyl-1,4-phenylene, ## top, # bottom) |
| Compound 1086 | 3-DBT | (2-methyl-1,4-phenylene, # top, ## bottom) | CA1 | Ph | (2-methyl-1,4-phenylene, ## top, # bottom) |
| Compound 1092 | 3-DBT | (2-methyl-1,4-phenylene, # top, ## bottom) | CA6 | Ph | (2-methyl-1,4-phenylene, ## top, # bottom) |
| Compound 1093 | 3-DBT | (2-methyl-1,4-phenylene, # top, ## bottom) | CA7 | Ph | (2-methyl-1,4-phenylene, ## top, # bottom) |

-continued
| Substituent of compound | Ar | L₁ | R₃ | R₄ | L₂ |
|---|---|---|---|---|---|
| Compound 1094 | 3-DBT | 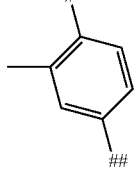 | CA8 | Ph | 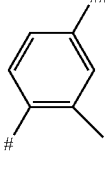 |
| Compound 1095 | 3-DBT | 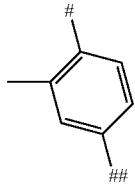 | CA9 | Ph | 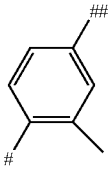 |
| Compound 1096 | 3-DBT | 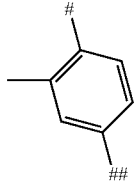 | CA10 | Ph | 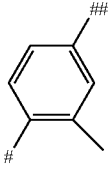 |
| Compound 1137 | 3-DBT | 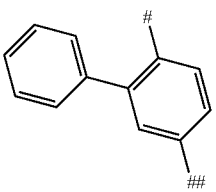 | CA1 | Ph | 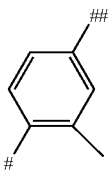 |
| Compound 1142 | 3-DBT | 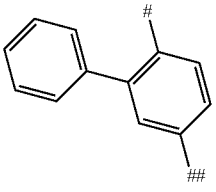 | CA6 | Ph | 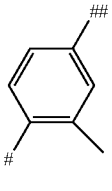 |
| Compound 1143 | 3-DBT | 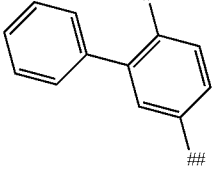 | CA7 | Ph | 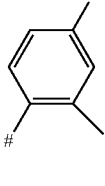 |
| Compound 1144 | 3-DBT | 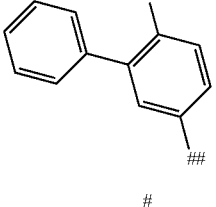 | CA8 | Ph | 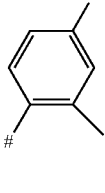 |
| Compound 1145 | 3-DBT | 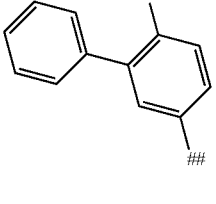 | CA9 | Ph | 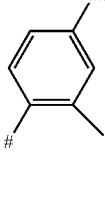 |

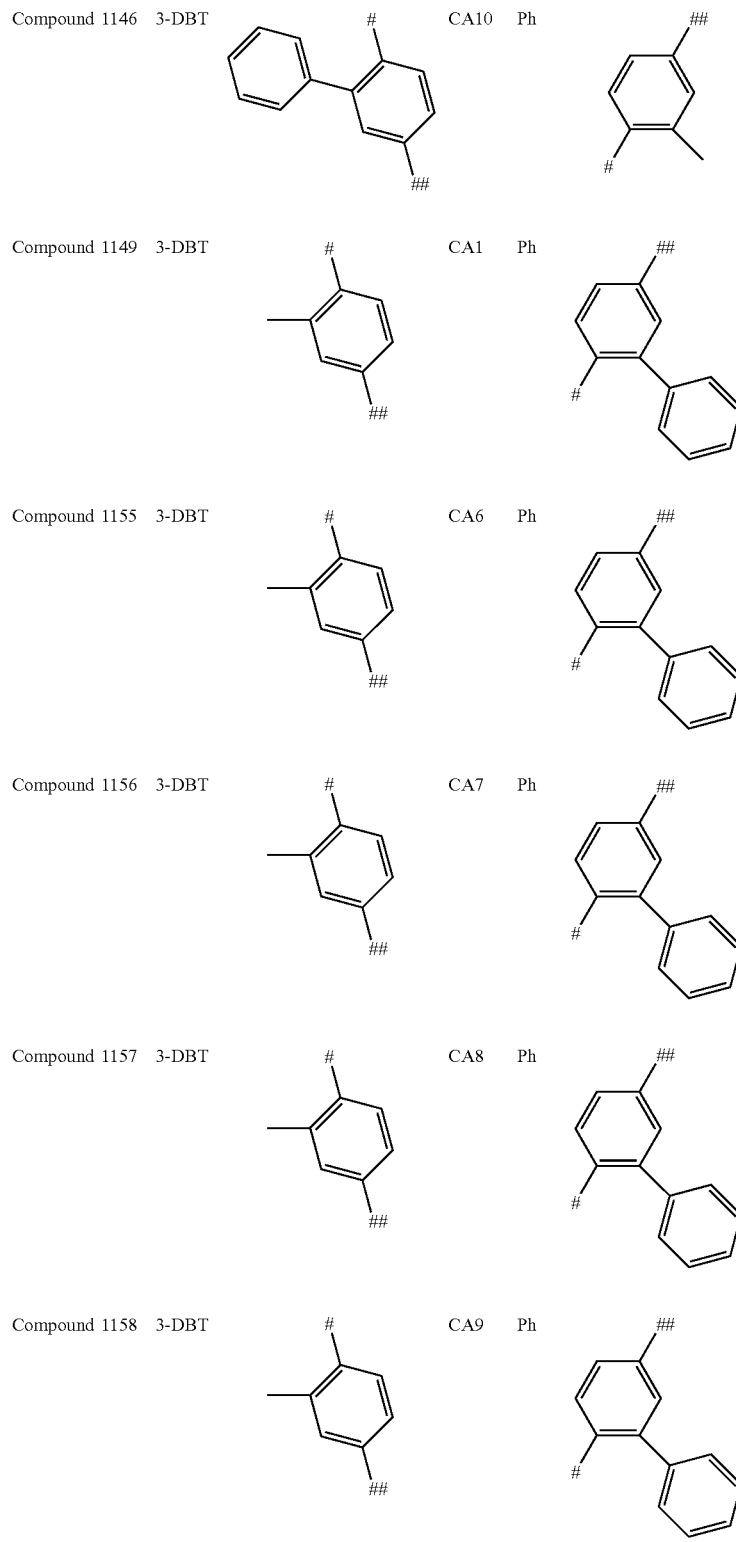

-continued

| Substituent of compound | Ar | L₁ | R₃ | R₄ | L₂ |
|---|---|---|---|---|---|
| Compound 1159 | 3-DBT | (methylphenylene) | CA10 | Ph | (biphenylene) |
| Compound 1162 | 3-DBT | (biphenylene) | CA1 | Ph | (biphenylene) |
| Compound 1169 | 3-DBT | (biphenylene) | CA6 | Ph | (biphenylene) |
| Compound 1170 | 3-DBT | (biphenylene) | CA7 | Ph | (biphenylene) |
| Compound 1171 | 3-DBT | (biphenylene) | CA8 | Ph | (biphenylene) |
| Compound 1172 | 3-DBT | (biphenylene) | CA9 | Ph | (biphenylene) |

-continued

| Substituent of compound | Ar | L₁ | R₃ | R₄ | L₂ |
|---|---|---|---|---|---|
| Compound 1173 | 3-DBT | (2-phenyl-phenyl, # at 2', ## at 5) | CA10 | Ph | (biphenyl, ## at top, # at bottom) |
| Compound 1218 | 3-DBT | (2-methylphenyl, # top, ## bottom) | H | CA1 | (methylphenyl, ## top, # bottom) |
| Compound 1223 | 3-DBT | (2-methylphenyl, # top, ## bottom) | H | CA6 | (methylphenyl, ## top, # bottom) |
| Compound 1224 | 3-DBT | (2-methylphenyl, # top, ## bottom) | H | CA7 | (methylphenyl, ## top, # bottom) |
| Compound 1227 | 3-DBT | (2-methylphenyl, # top, ## bottom) | H | CA8 | (methylphenyl, ## top, # bottom) |
| Compound 1228 | 3-DBT | (2-methylphenyl, # top, ## bottom) | H | CA9 | (methylphenyl, ## top, # bottom) |
| Compound 1229 | 3-DBT | (2-methylphenyl, # top, ## bottom) | H | CA10 | (methylphenyl, ## top, # bottom) |

-continued
| Substituent of compound | Ar | L₁ | R₃ | R₄ | L₂ |
|---|---|---|---|---|---|
| Compound 1258 | 3-DBT | 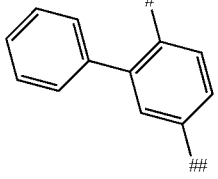 | H | CA1 | 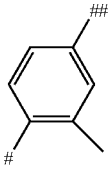 |
| Compound 1263 | 3-DBT | 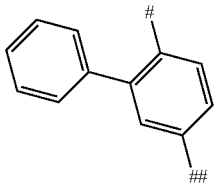 | H | CA6 | 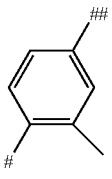 |
| Compound 1264 | 3-DBT | 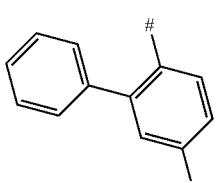 | H | CA7 | 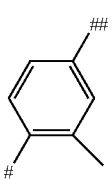 |
| Compound 1265 | 3-DBT | 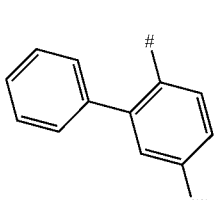 | H | CA8 | 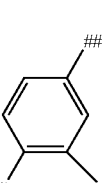 |
| Compound 1266 | 3-DBT | 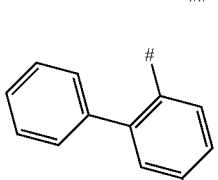 | H | CA9 | 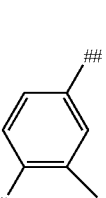 |
| Compound 1267 | 3-DBT | 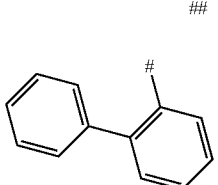 | H | CA10 | 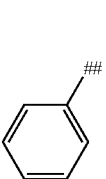 |
| Compound 1270 | 3-DBT | 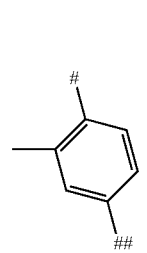 | H | CA1 | 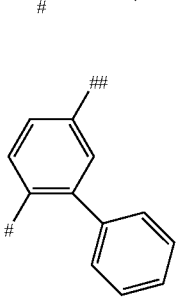 |

-continued
| Substituent of compound | Ar | L₁ | R₃ | R₄ | L₂ |
|---|---|---|---|---|---|
| Compound 1276 | 3-DBT | 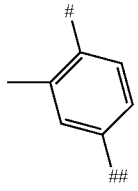 | H | CA6 | 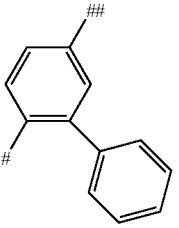 |
| Compound 1277 | 3-DBT | 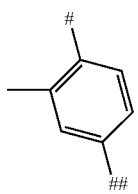 | H | CA7 | 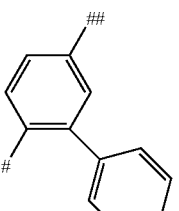 |
| Compound 1278 | 3-DBT | 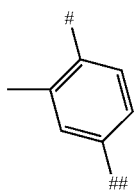 | H | CA8 | 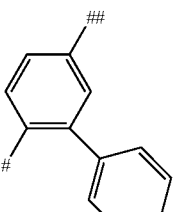 |
| Compound 1279 | 3-DBT | 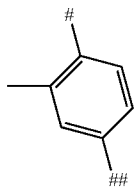 | H | CA9 | 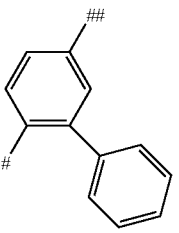 |
| Compound 1280 | 3-DBT | 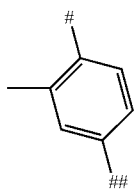 | H | CA10 | 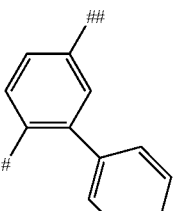 |
| Compound 1283 | 3-DBT | 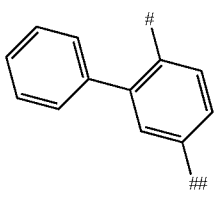 | H | CA1 | 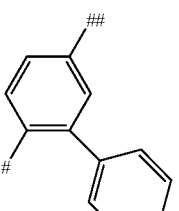 |

-continued

| Substituent of compound | Ar | L₁ | R₃ | R₄ | L₂ |
|---|---|---|---|---|---|
| Compound 1288 | 3-DBT | (structure) | H | CA6 | (structure) |
| Compound 1289 | 3-DBT | (structure) | H | CA7 | (structure) |
| Compound 1290 | 3-DBT | (structure) | H | CA8 | (structure) |
| Compound 1291 | 3-DBT | (structure) | H | CA9 | (structure) |
| Compound 1294 | 3-DBT | (structure) | H | CA10 | (structure) |

3. An electronic element, comprising an anode and a cathode which are arranged oppositely, and a functional layer arranged between the anode and the cathode,
 wherein the functional layer contains the nitrogen-containing compound according to claim 1.

4. The electronic element according to claim 3, wherein the functional layer comprises a hole transporting layer, and the hole transporting layer contains the nitrogen-containing compound.

5. The electronic element according to claim 4, wherein the hole transporting layer comprises a first hole transporting layer and a second hole transporting layer; the first hole transporting layer is arranged to be closer to the surface of the anode than the second hole transporting layer; and the first hole transporting layer or the second hole transporting layer contains the nitrogen-containing compound.

6. The electronic element according to claim 5, wherein the second hole transporting layer consists of the nitrogen-containing compound.

7. The electronic element according to claim 5, wherein the electronic element is a photoelectric conversion device or an organic electroluminescent device.

8. An electronic apparatus, comprising the electronic element according to claim 3.

9. An electronic element, comprising an anode and a cathode which are arranged oppositely, and a functional layer arranged between the anode and the cathode, wherein the functional layer contains the nitrogen-containing compound according to claim 2.

10. The electronic element according to claim 9, wherein the functional layer comprises a hole transporting layer, and the hole transporting layer contains the nitrogen-containing compound.

11. The electronic element according to claim 10, wherein the hole transporting layer comprises a first hole transporting layer and a second hole transporting layer; the first hole transporting layer is arranged to be closer to the surface of the anode than the second hole transporting layer; and the first hole transporting layer or the second hole transporting layer contains the nitrogen-containing compound.

12. The electronic element according to claim 11, wherein the second hole transporting layer consists of the nitrogen-containing compound.

13. The electronic element according to claim 11, wherein the electronic element is a photoelectric conversion device or an organic electroluminescent device.

14. An electronic apparatus, comprising the electronic element according to claim 9.

\* \* \* \* \*